(12) United States Patent
Tat et al.

(10) Patent No.: US 10,564,130 B2
(45) Date of Patent: *Feb. 18, 2020

(54) METHOD AND APPARATUS FOR ACOUSTIC EMISSIONS TESTING

(71) Applicant: The Boeing Company, Chicago, IL (US)

(72) Inventors: Hong Hue Tat, Redmond, WA (US); Yuan-Jye Wu, Issaquah, WA (US); Joseph D. Schaefer, St. Louis, MO (US); Anne Kao, Bellevue, WA (US); Mary J. Mathews, Brier, WA (US); Matthew G. Pike, St. Louis, MO (US); Victor P. Pauca, Winston-Salem, NC (US); Rongzhong Li, Winston-Salem, NC (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,937

(22) Filed: May 4, 2018

(65) Prior Publication Data

US 2018/0252680 A1    Sep. 6, 2018

Related U.S. Application Data

(63) Continuation-in-part of application No. 15/150,595, filed on May 10, 2016, now Pat. No. 9,989,501.

(51) Int. Cl.
*G01N 29/46*    (2006.01)
*G01N 29/14*    (2006.01)
*G01N 29/44*    (2006.01)

(52) U.S. Cl.
CPC ............. *G01N 29/14* (2013.01); *G01N 29/46* (2013.01); *G01N 29/4445* (2013.01)

(58) Field of Classification Search
CPC ..... G01N 29/14; G01N 29/46; G01N 29/4445
USPC ......................................................... 73/587
See application file for complete search history.

(56) References Cited

U.S. PATENT DOCUMENTS

| 5,528,557 | A | 6/1996 | Horn |
| 5,814,729 | A | 9/1998 | Wu et al. |

(Continued)

FOREIGN PATENT DOCUMENTS

| EP | 0317322 A2 | 5/1989 |
| EP | 3244204 A1 | 11/2017 |
| WO | WO2010027978 A1 | 3/2010 |

OTHER PUBLICATIONS

European Patent Office Search Report, dated Oct. 18, 2017, regarding Application No. 17167161.3, 7 pages.

(Continued)

*Primary Examiner* — Jacques M Saint Surin
(74) *Attorney, Agent, or Firm* — Yee & Associates, P.C.

(57) ABSTRACT

An apparatus comprises an acoustic sensing system and an analyzer module. The acoustic sensing system is positioned relative to an object, wherein the acoustic sensing system detects acoustic emissions and generates acoustic waveform data for the acoustic emissions detected. The analyzer module is implemented in a computer system that receives load data and the acoustic waveform data for the object, generates a plurality of frequency distribution functions using the acoustic waveform data, and generates a frequency distribution function time evolution image containing a plurality of points of each of the plurality of frequency distribution functions.

22 Claims, 18 Drawing Sheets

(56) References Cited

U.S. PATENT DOCUMENTS

| | | | |
|---|---|---|---|
| 6,386,038 B1 | 5/2002 | Lewis et al. | |
| 7,546,224 B2* | 6/2009 | Campbell | G05B 17/02 |
| | | | 702/33 |
| 7,930,112 B2* | 4/2011 | Mattes | G01M 5/0016 |
| | | | 702/36 |
| 8,015,876 B2 | 9/2011 | El-Bakry et al. | |
| 8,186,223 B2* | 5/2012 | Dawson | G01M 15/12 |
| | | | 73/587 |
| 8,661,902 B2* | 3/2014 | El-Bakry | G01L 1/255 |
| | | | 73/587 |
| 8,826,738 B2 | 9/2014 | El-Bakry et al. | |
| 9,989,501 B2* | 6/2018 | Tat | G01N 29/14 |
| 2008/0059086 A1 | 3/2008 | Ziyad et al. | |
| 2017/0328868 A1 | 11/2017 | Tat et al. | |

OTHER PUBLICATIONS

Vi-Tong et al., "An algorithm for non-supervised sequential classification for signals", Pattern Recognition Letter, No. 5, May 1987, 7 pages.

Gutkin et al., "On acoustic emission for failure investigation in CFRP: Pattern recognition and peak frequency analyses," Mechanical Systems and Signal Processing, vol. 25, May 2011, 15 pages.

Maillet et al., "Waveform-based selection of acoustic emission events generated by damage in composite materials," Mechanical Systems and Signal Processing, vols. 52-53, Feb. 2015, 11 pages.

McCrory et al., "Damage classification in carbon fibre composites using acoustic emission: A comparison of three techniques," Composites: Part B, vol. 68, Jan. 2015, 7 pages.

Martinez-Jequier et al., "Real-time damage mechanisms assessment in CFRP samples via acoustic emission Lamb wave modal analysis," Composite: Part B, vol. 68, Jan. 2015, 10 pages.

European Patent Office Extended Search Report, dated Sep. 20 2019, regarding Application No. 19172638.9, 11 pages.

Loutas et al., "Damage Evolution in Center-Holed Glass/Polyester Composites Under Quasi-Static Loading Using Time/Frequency Analysis of Acoustic Emission Monitored Waveforms," Composites Science and Technology, vol. 66, Issue 10, Amsterdam, NL, Aug. 2006, pp. 1366-1375.

\* cited by examiner

METHOD AND APPARATUS FOR ACOUSTIC EMISSIONS TESTING

CROSS-REFERENCE TO RELATED APPLICATION

This application is a continuation-in-part application of U.S. patent application Ser. No. 15/150,595, filed May 10, 2016, now U.S. Pat. No. 9,989,501, issued Jun. 5, 2018.

BACKGROUND INFORMATION

1. Field

The present disclosure relates generally to acoustic emissions and, in particular, to detecting acoustic emissions from objects. Still more particularly, the present disclosure relates to a method and apparatus for analyzing acoustic emissions of objects to assess the structural integrity of these objects over time.

2. Background

Acoustic emission is the radiation of acoustic waves in an object or material when the material undergoes a structural change. For example, without limitation, acoustic emissions may occur when a composite object undergoes a structural change. This structural change may take the form of a crack forming, a crack extending, a split forming, a split extending, delamination, some other type of structural change, or a combination thereof.

These acoustic waves may be detected using acoustic sensors that are used to generate data that can then be analyzed. However, identifying the nature or method of structural change with a desired level of accuracy using currently available methods for performing acoustic emissions detection and analysis may be more difficult, tedious, and time-consuming than desired. In some cases, identifying the nature or mode of structural change may not be possible using currently available methods.

Some currently available methods of acoustics emissions detection and testing may require that the signals generated based on the acoustic emissions detected be the result of a single type of structural event. However, some objects such as, but not limited to, composite objects, may simultaneously undergo multiple types of structural change. Some currently available methods of acoustic detection and testing may be unable to easily and quickly determine when multiple modes of structural change are occurring simultaneously. In particular, when multiple structural changes occur in an object during a given time interval, currently available methods of acoustic detection and testing may be unable to identify the specific modes of structural change. Therefore, it would be desirable to have a method and apparatus that take into account at least some of the issues discussed above, as well as other possible issues.

SUMMARY

In one illustrative embodiment, an apparatus is presented. The apparatus comprises an acoustic sensing system and an analyzer module. The acoustic sensing system is positioned relative to an object. The acoustic sensing system detects acoustic emissions and generates acoustic waveform data for the acoustic emissions detected. The analyzer module is implemented in a computer system that receives load data and the acoustic waveform data for the object, generates a plurality of frequency distribution functions using the acoustic waveform data, and generates a frequency distribution function time evolution image containing a plurality of points of each of the plurality of frequency distribution functions.

In another illustrative embodiment, a method for analyzing an object using acoustic waves is presented. Load data for the object is received. Acoustic waveform data for the object is received from an acoustic sensing system, wherein the acoustic waveform data represents acoustic emissions emanating from the object and is detected using the acoustic sensing system. A plurality of frequency distribution functions is generated using the acoustic waveform data. A frequency distribution function time evolution image containing a plurality of points of each of the plurality of frequency distribution functions is generated.

In yet another illustrative embodiment, a method is presented. Acoustic emissions radiating from an object are detected using an acoustic sensing system to generate acoustic waveform data. A plurality of frequency distribution functions are generated, by an analyzer module, using the acoustic waveform data, wherein each of the plurality of frequency distribution functions has an identifier of either a respective time or a respective load. An array is created that has a quantity of columns equivalent to a quantity of frequency distribution functions in the plurality of frequency distribution functions and a quantity of rows equivalent to a quantity of frequency bins in each frequency distribution function of the plurality of frequency distribution functions. The array is filled such that a plurality of points of each of the plurality of frequency distribution functions is contained within the array, in which the array allows the analyzer module to identify structural changes in the object previously unidentifiable by an operator using frequency plots containing a single point for each waveform of the acoustic waveform data.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
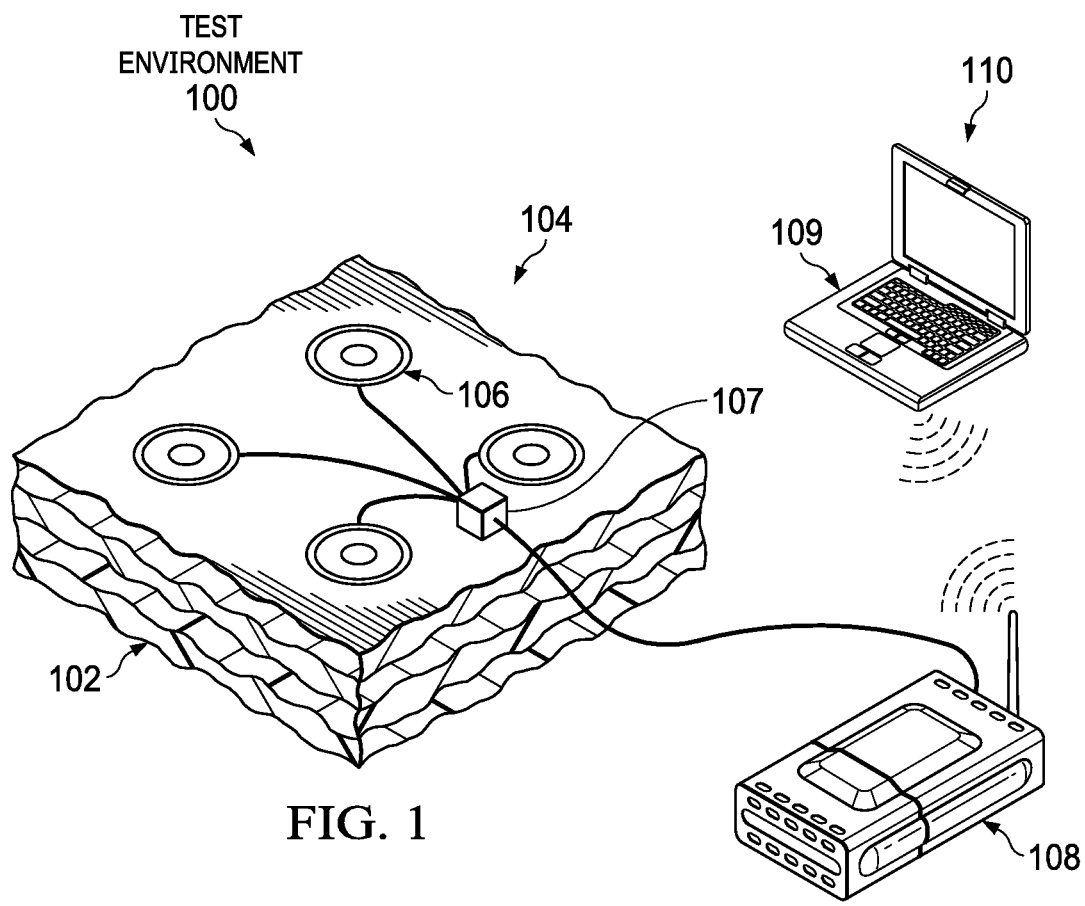
FIG. 1 is an illustration of a test environment in accordance with an illustrative embodiment.

The illustrative embodiments take into account different considerations. For example, the illustrative embodiments take into account that it may be desirable to have a method and apparatus for detecting and analyzing acoustic emissions from objects that enable the identification and classification of multiple structural events that are occurring simultaneously. In particular, the illustrative embodiments take into account that it may be desirable to have a method and apparatus for analyzing acoustic emissions relative to the load history of an object that allows for accurate correlation between acoustic waveforms and specific modes of structural change.

Thus, the illustrative embodiments provide a method and apparatus for analyzing an object using acoustic emissions. In one illustrative example, acoustic emissions emanating from the object are detected using an acoustic sensing system to generate acoustic waveform data. The acoustic waveform data is received along with load data for the object. A plurality of bins is created for the load data. A plurality of frequency distribution functions is generated for the plurality of bins using the acoustic waveform data. A set of learning algorithms is applied to the plurality of frequency distribution functions to generate an output that allows an operator to more easily and quickly assess a structural integrity of the object.

In particular, the illustrative embodiments provide a method and apparatus that solves the challenges associated with determining when multiple modes of structural change occur in an object simultaneously. Further, the illustrative embodiments provide a method and apparatus that solves the challenges associated with identifying each specific mode of structural change that occurs in an object during a given time interval even when multiple modes of structural change occur during that time interval.

The illustrative embodiments take into account that in traditional frequency plots for acoustic emission data, such as point plots of maximum frequency versus time, some signal features are masked or lost. The illustrative embodiments take into account that unidentified peaks correlate to unidentified structural changes.

The illustrative embodiments provide a method and apparatus that identify structural changes previously unidentified by operators in conventional processes. The illustrative embodiments, in some cases, provide a method and apparatus to more efficiently use acoustic waveform data to identify previously unidentified structural changes. The illustrative embodiments provide a method and apparatus to more efficiently find patterns in acoustic waveform data to identify previously unidentified structural changes.

The illustrative embodiments provide a method and apparatus that will reduce testing costs and reduce cycle time for manufacturing components. The illustrative embodiments provide a method and apparatus that may be used in developing new materials. Behavioral characteristics and structural changes of the new materials identified by the illustrative embodiments will have greater certainty than conventional methods.

Referring now to the figures and, in particular, with reference to FIG. 1, an illustration of a test environment is depicted in accordance with an illustrative embodiment. In this illustrative example, test environment 100 may be used to perform testing of object 102. In this illustrative example, object 102 takes the form of a composite object. However, in other illustrative examples, object 102 may be some other type of object, such as, but not limited to, a metallic object.

Acoustic sensing system 104 is used to detect acoustic emissions emanating from object 102. Acoustic sensing system 104 includes acoustic sensors 106, signal conditioner 107, and transmitter 108. Each acoustic sensor of acoustic sensors 106 is positioned in contact with object 102 and is capable of detecting acoustic waves that may radiate through object 102 over time as a load is applied to object 102. This load (not shown) may be constant over time, may vary over time, or may follow a pattern of constant intervals mixed with varying intervals over time.

In this illustrative example, acoustic sensors 106 generate acoustic emissions signals that are sent through signal conditioner 107 to transmitter 108. Signal conditioner 107 may amplify, filter, both amplify and filter these acoustic emissions signals. Transmitter 108 may then convert the acoustic emissions signals into acoustic waveform data that is then wirelessly transmitted to analyzer module 109 for processing. In some cases, transmitter 108 includes a preamplifier or amplifier component that may adjust the gain of the acoustic emissions signals before conversion into the acoustic waveform data.

As depicted, analyzer module 109 is implemented in computer system 110. In this illustrative example, transmitter 108 wirelessly sends the acoustic waveform data to analyzer module 109 in computer system 110. In other illustrative examples, transmitter 108 may send the acoustic waveform data to analyzer module 109 over one or more wired connections.

Analyzer module 109 receives both the acoustic waveform data and load data. The load data may include measurements of the load being applied to or the load being experienced by object 102 over time. Analyzer module 109 processes the acoustic waveform data and the load data in a manner that reduces the amount of time and computer processing resources needed to identify the nature and modes of structural change in object 102 over time based on the acoustic emissions detected. In particular, analyzer module 109 generates an output that allows an operator to more easily and quickly assess a structural integrity of object 102.

Figure 2:
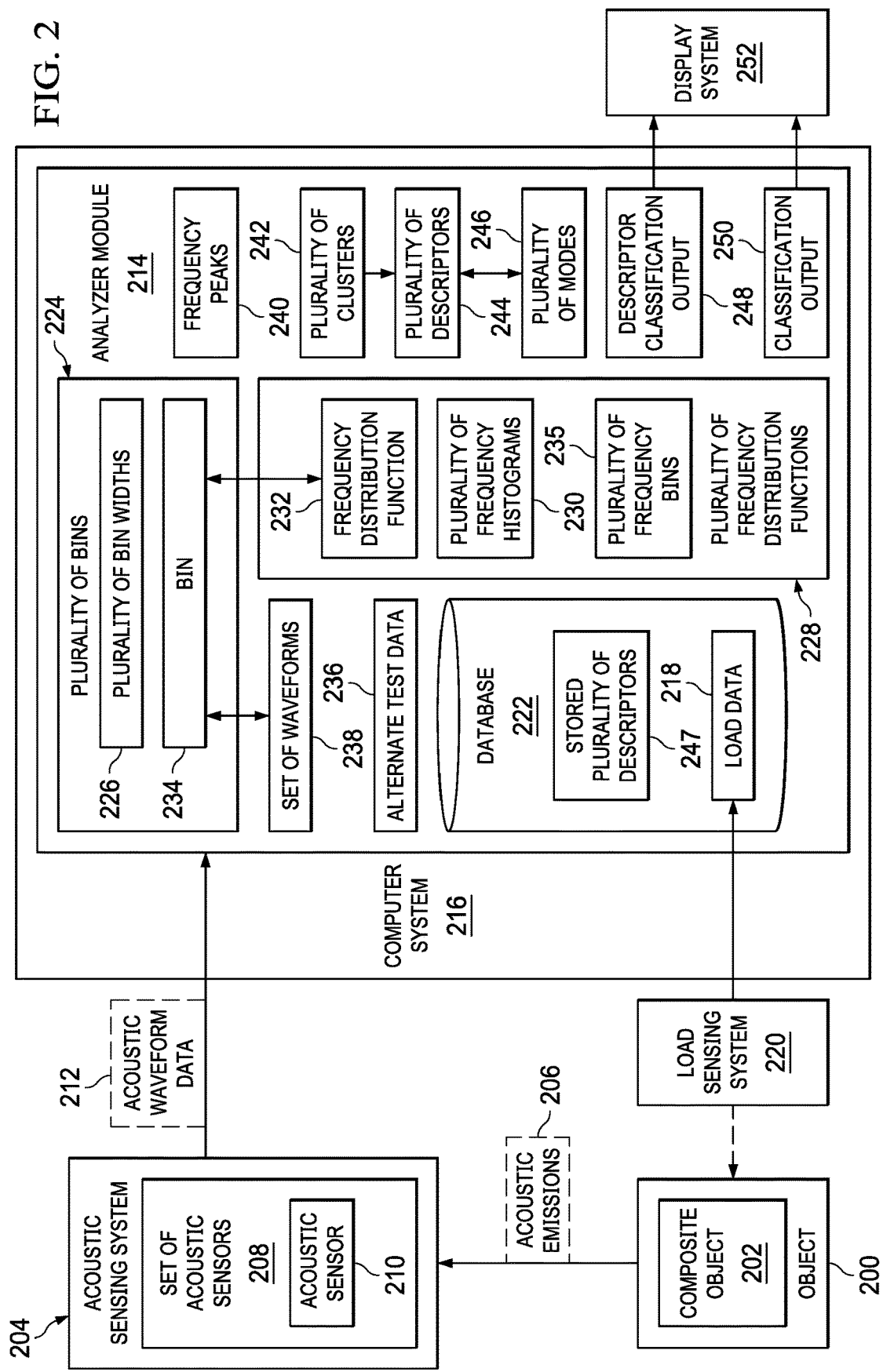
FIG. 2 is an illustration of an object, an acoustic sensing system, and an analyzer module in the form of a block diagram in accordance with an illustrative embodiment.

With reference now to FIG. 2, an illustration of an object, an acoustic sensing system, and an analyzer module is depicted in the form of a block diagram in accordance with an illustrative embodiment. Object 200 may take a number of different forms. In one illustrative example, object 200 takes the form of composite object 202. However, in other illustrative examples, object 200 may take the form of a metal object, an object having at least a partial metallic composition, or some other type of object.

Depending on the implementation, object 200 may be at any stage in the lifecycle of object 200. For example, without limitation, object 200 may be in a testing stage, in a system integration stage, in an in-service stage, in a maintenance stage, in a repair stage, or at some other point in time during the lifecycle of object 200. In one illustrative example, composite object 202 may be a composite test coupon. Object 102 in FIG. 1 is an example of one implementation for object 200 in FIG. 2.

Acoustic sensing system 204 is used to detect acoustic emissions 206 from object 200 in response to the loading of object 200. This loading may be performed in a number of different ways, depending on the implementation. For example, in some cases, an external load may be applied to object 200 for an extended period of time, while acoustic sensing system 204 is used to detect acoustic emissions 206 that result due to this loading. In other illustrative examples, the loading may be due to the integration of object 200 into a larger structure or system.

The loading of object 200 may affect the structural integrity of object 200 over time. For example, the loading may cause certain structural changes in object 200 that reduce the structural integrity of object 200. These structural changes may include, but are not limited to, crack formation, splitting, the extension of cracks, the extension of splits, fiber breakage, delamination, some other type of undesired structural change, or a combination thereof.

Acoustic emissions 206 are acoustic waves that radiate through object 200 due to structural changes in object 200. Acoustic sensing system 204 comprises set of acoustic sensors 208. As used herein, a "set of" items may include one or more items. In this manner, set of acoustic sensors 208 may include one or more acoustic sensors.

Acoustic sensor 210 is an example of one acoustic sensor in set of acoustic sensors 208. In one illustrative example, acoustic sensor 210 is positioned in contact with object 200 to detect acoustic emissions 206.

Set of acoustic sensors 208 detect acoustic emissions 206 and generate acoustic waveform data 212 for acoustic emissions 206 detected. Acoustic waveform data 212 is sent to analyzer module 214. Analyzer module 214 may receive acoustic waveform data 212 from acoustic sensing system 204 using any number of wired communications links, wireless communications links, other types of communications links, or a combination thereof.

In this illustrative example, analyzer module 214 may be implemented in software, hardware, firmware, or a combination thereof. When software is used, the operations performed by analyzer module 214 may be implemented using, for example, without limitation, program code configured to run on a processor unit. When firmware is used, the operations performed by analyzer module 214 may be implemented using, for example, without limitation, program code and data and stored in persistent memory to run on a processor unit.

When hardware is employed, the hardware may include one or more circuits that operate to perform the operations of analyzer module 214. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In this illustrative example, analyzer module 214 is implemented using computer system 216. Analyzer module 109 implemented in computer system 110 in FIG. 1 may be an example of one implementation for analyzer module 214 implemented in computer system 216. Computer system 216 may include a single computer or multiple computers in communication with each other.

In addition to receiving acoustic waveform data 212, analyzer module 214 also receives load data 218. In one illustrative example, load data 218 may be data generated by load sensing system 220. Load sensing system 220 may include one or more load sensors that measure the loading of object 200 over time.

In other illustrative examples, analyzer module 214 retrieves load data 218 from database 222. For example, without limitation, load data 218 may be previously generated load data that was generated for an object similar to object 200 under the same or similar loading conditions.

Analyzer module 214 creates plurality of bins 224 for load data 218. Plurality of bins 224 has plurality of bin widths 226. In particular, each bin in plurality of bins 224 has a corresponding bin width in plurality of bin widths 226. In one illustrative example, plurality bin widths 226 may be equal. However, in other illustrative examples, one or more bin widths of plurality of bin widths 226 may be different.

In some illustrative examples, plurality of bin widths 226 is a plurality of time-based bin widths. In other words, each bin of plurality of bins 224 may correspond to a time interval. In other illustrative examples, plurality of bin widths 226 is a plurality of load-based bin widths. In other words, each bin of plurality of bins 224 may correspond to a load interval.

Analyzer module 214 generates plurality of frequency distribution functions 228 using plurality of bins 224 and acoustic waveform data 212. In one illustrative example, plurality of frequency distribution functions 228 takes the form of plurality of frequency histograms 230.

Plurality of frequency distribution functions 228 includes one frequency distribution function for each bin in plurality of bins 224. For example, analyzer module 214 generates frequency distribution function 232 for bin 234. Bin 234 has a defined bin width that may be a defined time interval or a defined load interval.

In one illustrative example, analyzer module 214 creates frequency distribution function 232 by dividing a selected frequency range into plurality of frequency bins 235. Depending on the implementation, plurality of frequency bins 235 may have the same or different bin widths. Each frequency bin in plurality of frequency bins 235 is used to hold a count and therefore can be incremented.

Analyzer module 214 then processes acoustic waveform data 212 relative to load data 218. For example, for each bin in plurality of bins 224, analyzer module 214 identifies a set of waveforms that fall within that bin using acoustic waveform data 212. Thereafter, analyzer module 214 computes a Fast Fourier Transform for the set of waveforms identified for each bin in plurality of bins 224.

As one illustrative example, analyzer module 214 identifies set of waveforms 238 that falls within bin 234 using acoustic waveform data 212. In some illustrative examples, plurality of bin widths 226 for plurality of bins 224 may be selected such that at least one waveform falls entirely within each bin of plurality of bins 224. Next, analyzer module 214 computes a Fast Fourier Transform for set of waveforms 238 that falls within bin 234. Analyzer module 214 then identifies frequency peaks 240 for set of waveforms 238 based on the Fast Fourier Transform computed.

In one illustrative example, analyzer module 214 selects a defined number of frequency peaks for each waveform in set of waveforms 238. As used herein, a "number of" items may include one or more items. In this manner, a defined number of frequency peaks may include one or more frequency peaks. In some cases, the number of frequency peaks selected by analyzer module 214 may be, for example, without limitation, three, four, five, eight, or some other number of frequency peaks for each waveform in set of waveforms 238 based on the Fast Fourier Transformer computed for set of waveforms 238.

Analyzer module 214 increments a corresponding frequency bin in plurality of frequency bins 235 when a frequency peak that has been identified falls within the corresponding frequency bin. For example, if any of frequency peaks 240 falls within the frequency bin corresponding to the range of about 80 kilohertz to about 90 kilohertz, then the frequency bin is incremented by the total number of frequency peaks falling within this range. This process creates frequency distribution function 232 for bin 234.

In other illustrative examples, plurality of frequency bins 235 may be accumulated differently. For example, a frequency bin in plurality of frequency bins 235 may be an accumulation of energy at that frequency bin, computed using acoustic waveform data 212.

The process of creating frequency distribution function 232 for bin 234 is repeated for each of plurality of bins 224 to ultimately create plurality of frequency distribution functions 228. Plurality of frequency distribution functions 228 provide an operator with an easy way to quickly assess the structural integrity of object 200.

When object 200 is a test object, further processing of plurality of frequency distribution functions 228 is performed by analyzer module 214. For example, without limitation, analyzer module 214 creates plurality of clusters 242 using plurality of frequency distribution functions 228. Plurality of clusters 242 is a plurality of clusters of interest.

In one illustrative example, analyzer module 214 applies one or more unsupervised learning algorithms to plurality of frequency distribution functions 228 to establish plurality of clusters 242. Each cluster in plurality of clusters 242 is a grouping of frequency distribution functions from plurality of frequency distribution functions 228.

As used herein, an unsupervised learning algorithm is a machine learning algorithm for drawing inferences from datasets comprising data without labeled responses. One example of unsupervised learning is clustering. A clustering algorithm may be an algorithm for grouping a set of elements in such a way that elements in the same group, which may be referred to as a cluster, are more similar to each other than to those in other groups.

In these illustrative examples, analyzer module 214 may use a set of unsupervised learning algorithms to group frequency distribution functions in plurality of frequency distribution functions 228 to form plurality of clusters 242. Depending on the implementation, a k-means clustering algorithm, a mixture model clustering algorithm, a hierarchical clustering algorithm, some other type of clustering algorithm, some other type of unsupervised learning algorithm, or a combination thereof may be used to identify plurality of clusters 242.

Each cluster in plurality of clusters 242 corresponds to a structural change that affects the structural integrity of object 200. In one illustrative example, each cluster in plurality of clusters 242 corresponds to a different mode of structural change that reduces the structural integrity of object 200.

In one illustrative example, analyzer module 214 identifies plurality of descriptors 244 for plurality of clusters 242. A descriptor for a cluster may be a centroid, a mean, or some other type of representative frequency distribution function for the cluster. As one illustrative example, the descriptor may be the centroid frequency distribution function for that cluster.

Plurality of clusters 242 may be associated with a plurality of modes of structural change using alternate test data 236. Alternate test data 236 may be data from which structural changes in object 200 may be readily identified. For example, alternate test data 236 may take the form of x-ray imaging data, ultrasound imaging data, infrared imaging data, modeling data, or some other type of data. The modeling data may be generated from a computer model.

As one illustrative example, without limitation, alternate test data 236 takes the form of in-situ x-ray data generated for object 200 during the loading of object 200. Alternate test data 236 is then used to detect structural changes in object 200 and identify these structural changes as plurality of modes 246. Each mode in plurality of modes 246 may be a different type of structural change. In some cases, each mode in plurality of modes 246 may be referred to as a mode of structural compromise.

For example, without limitation, when object 200 takes the form of a composite test coupon, plurality of modes 246 may include crack formation, crack extension, splitting, and split extension. In some cases, plurality of modes 246 may also include fiber breakage, delamination, or some other form of structural compromise.

Both plurality of modes 246 and plurality of clusters 242 are mapped back to load data 218 such that each cluster in plurality of clusters 242 substantially overlaps with a corresponding mode in plurality of modes 246. In other words, plurality of modes 246 may be mapped backed to specific times, load conditions, or both using load data 218.

Similarly, plurality of clusters 242 may be mapped back to specific times, load conditions, or both using load data 218. For example, without limitation, each bin in plurality of bins 224 for load data 218 may be designated as holding one or more waveforms that belong to a particular cluster in plurality of clusters 242.

In one illustrative example, each cluster of plurality of clusters 242 may substantially overlap, or overlap within selected tolerances, with a corresponding mode in plurality of modes 246 with respect to time. In this manner, each cluster in plurality of clusters 242 may be paired with or assigned to a corresponding mode in plurality of modes 246. In one illustrative example, the descriptor corresponding to each cluster in plurality of clusters 242 is paired with a corresponding mode in plurality of modes 246. In other words, plurality of descriptors 244 may be paired with plurality of modes 246.

In one illustrative example, plurality of clusters 242 may include a first cluster having a first descriptor, a second cluster having a second descriptor, a third cluster having a third descriptor, and a fourth cluster having a fourth descriptor. In this illustrative example, the first cluster and the first descriptor represent a first mode of structural change. The second cluster and the second descriptor represent a second mode of structural change. The third cluster and the third descriptor represent a third mode of structural change. The fourth cluster and the fourth descriptor represent a fourth mode of structural change. Of course, in other illustrative examples, plurality of clusters 242 may include fewer than four clusters or more than four clusters.

Once each cluster in plurality of clusters 242 has been associated with a corresponding mode of structural change, plurality of descriptors 244 for plurality of clusters 242 is stored for future use. For example, plurality of descriptors 244 may be stored in database 222, or some other type of data structure or data storage, along with the mode classification for each descriptor.

In one illustrative example, analyzer module 214 generates descriptor classification output 248 that identifies the pairing of each mode in plurality of modes 246 with a corresponding descriptor in plurality of descriptors 244. Descriptor classification output 248 may be stored in database 222, or in some other data structure or data storage, for future use. In this manner, descriptor classification output 248 establishes baseline data that may be used to evaluate the structural integrity of one or more parts that are structurally the same as or structurally similar to object 200.

In other illustrative examples, object 200 may not be a test object. Rather, object 200 may be at an in-service stage, a maintenance stage, a repair stage, a certification stage, or some other type of stage in the lifecycle of object 200. In these illustrative examples, once plurality of frequency distribution functions 228 has been generated, analyzer module 214 applies one or more supervised learning algorithms to plurality of frequency distribution functions 228.

As used herein, a supervised learning algorithm is a machine learning algorithm for drawing inferences from labeled training data. In these illustrative examples, this labeled training data takes the form of descriptor classification output 248 that labels each descriptor in plurality of descriptors 244, which corresponds with a cluster in plurality of clusters 242, with a corresponding mode of plurality of modes 246.

A support vector machine is an example of one type of supervised learning algorithm. For example, without limitation, a support vector machine may be applied to plurality of frequency distribution functions 228 and stored plurality of descriptors 247 to generate classification output 250. Stored plurality of descriptors 247 is generated in a manner similar to plurality of descriptors 244. Stored plurality of descriptors 247 may be stored in database 222 or some other type of data structure or data storage.

In particular, a binary decision is made for each bin in plurality of bins 224 based on stored plurality of descriptors 247. More specifically, the frequency distribution function generated for each bin in plurality of bins 224 is analyzed relative to each descriptor in plurality of descriptors 244.

For example, without limitation, frequency distribution function 232 for bin 234 may be analyzed relative to each descriptor in stored plurality of descriptors 247. A determination is made as to whether frequency distribution function 232 matches the descriptor within selected tolerances or not. If frequency distribution function 232 matches the descriptor within selected tolerances, then set of waveforms 238 that fall within bin 234 may be classified as representing the mode that corresponds to that descriptor. This decision is performed for each descriptor in stored plurality of descriptors 247.

Because this type of binary decision is being made for each descriptor in stored plurality of descriptors 247, the each bin in plurality of bins 224 may be classified as representing multiple modes of structural change. In this manner, the set of waveforms that fall within any given bin of plurality of bins 224 may be classified as representing one or more modes of structural change. In some cases, the set of waveforms in a particular bin may be determined to not represent any particular mode in plurality of modes 246.

In one illustrative example, analyzer module 214 generates classification output 250 that includes a classification of each bin in plurality of bins 224 using one or more modes of plurality of modes 246 based on the analysis described above. In other illustrative examples, analyzer module 214 generates classification output 250 that identifies the classification of each waveform in acoustic waveform data 212 using one or more modes of plurality of modes 246.

Thus, the illustrative embodiments provide an accurate and efficient method for assessing the structural integrity of object 200. The information obtained based on this type of assessment may be used to then make decisions about object 200 with respect to certification, maintenance, repair, system integration, some other type of task, or a combination thereof.

The processing performed by analyzer module 214 may be easily tailored for different types of objects and loading conditions. As one illustrative example, plurality of bin widths 226 may be selected based on the type of loading of object 200. For example, without limitation, when object 200 is loaded more quickly, acoustic emissions 206 may occur more rapidly. Plurality of bin widths 226 may be selected to create smaller bins to allow for clearer separation of events. However, when object 200 is loaded more slowly, acoustic emissions 206 may occur more slowly. Plurality of bin widths 226 may then be selected to create larger bins to thereby reduce the overall volume of data that needs to be processed.

Further, in some illustrative examples, analyzer module 214 may be configured to display descriptor classification output 248, classification output 250, or both through a graphical user interface on display system 252. In some cases, plurality of frequency distribution functions 228 may be displayed on display system 252. In this manner, an operator may able to quickly and easily make decisions about object 200.

The illustration of object 200, acoustic sensing system 204, and analyzer module 214 in FIG. 2 is not meant to imply physical or architectural limitations to the manner in which an illustrative embodiment may be implemented.

Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, without limitation, in some cases, acoustic sensing system 204 may include at least one signal conditioner (not shown), such as signal conditioner 107 in FIG. 1, and a transmitter (not shown), such as transmitter 108 in FIG. 1. As one illustrative example, a signal conditioner may be used to amplify and filter the frequency content of the acoustic emissions signal detected by acoustic sensor 210. The acoustic emissions signal may then be converted into acoustic waveform data 212 by a transmitter sends acoustic waveform data 212 to analyzer module 214. The transmitter may send acoustic waveform data 212 to analyzer module 214 using one or more wireless communications links, wired communications links, or other type of communications links.

In some cases, a single signal conditioner may be used for amplifying and filtering the set of acoustic emissions signals generated by set of acoustic sensors 208. In other illustrative examples, each acoustic sensor in set of acoustic sensors 208 may be connected to a different signal conditioner. In still other illustrative examples, a signal conditioner may be integrated as part of each acoustic sensor in set of acoustic sensors 208.

Further, although classification output 250 is described as being generated using one or more supervised learning algorithms, in other illustrative examples, a semi-supervised learning algorithm or a process that combines supervised and unsupervised learning may be used to generate classification output 250. Still further, although descriptor classification output 248 is described as being generated using one or more unsupervised learning algorithms, in other illustrative examples, a semi-supervised learning algorithm or a process that combines supervised and unsupervised learning may be used to generate descriptor classification output 248.

Figure 3:
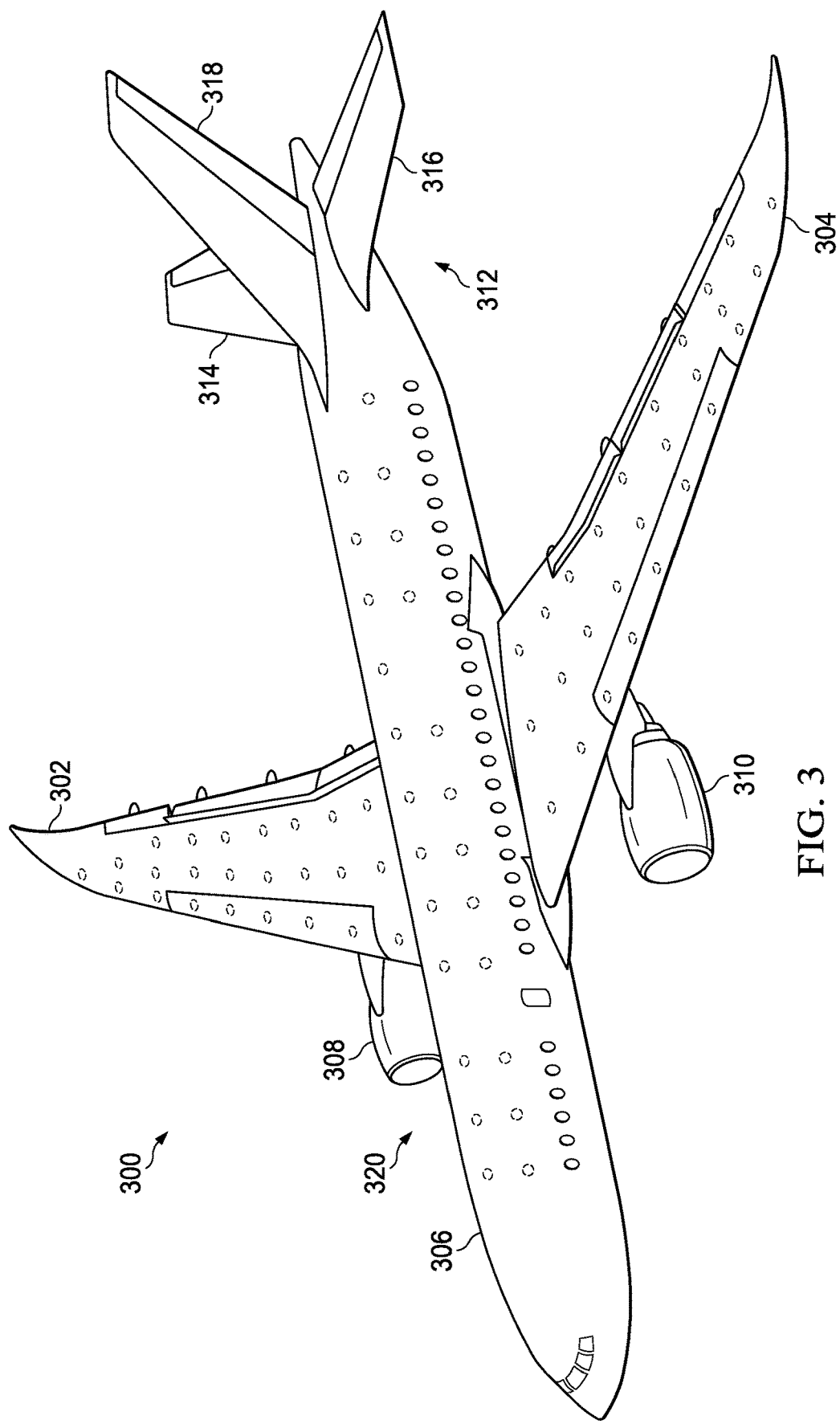
FIG. 3 is an illustration of an isometric view of an aircraft in accordance with an illustrative embodiment.

With reference now to FIG. 3, an illustration of an isometric view of an aircraft is depicted in accordance with an illustrative embodiment. In this illustrative example, aircraft 300 includes wing 302 and wing 304 attached to fuselage 306. Aircraft 300 also includes engine 308 attached to wing 302 and engine 310 attached to wing 304.

Further, aircraft 300 includes tail section 312. Horizontal stabilizer 314, horizontal stabilizer 316, and vertical stabilizer 318 are attached to tail section 312.

An acoustic sensing system (not shown), such as acoustic sensing system 204 in FIG. 2 or acoustic sensing system 104 in FIG. 1, may be positioned relative to aircraft 300 to monitor the acoustic emissions of various parts of aircraft 300 during the lifecycle of aircraft 300. For example, without limitation, the acoustic sensing system may include various acoustic sensors (not shown) at locations 320 along aircraft 300. Locations 320 may include locations that are in contact with a surface of a part of aircraft 300, embedded within a part or structure of aircraft 300, positioned near but not in contact with a part or structure of aircraft 300, or a combination thereof.

At any stage during the lifecycle of aircraft 300, the acoustic waveform data generated by the acoustic sensing system 204 may be collected and analyzed by analyzer module 214 in FIG. 2. In this manner, the structural integrity of the various parts or structures of aircraft 300 may be analyzed and any detected undesired structural changes may be classified.

Figure 4:
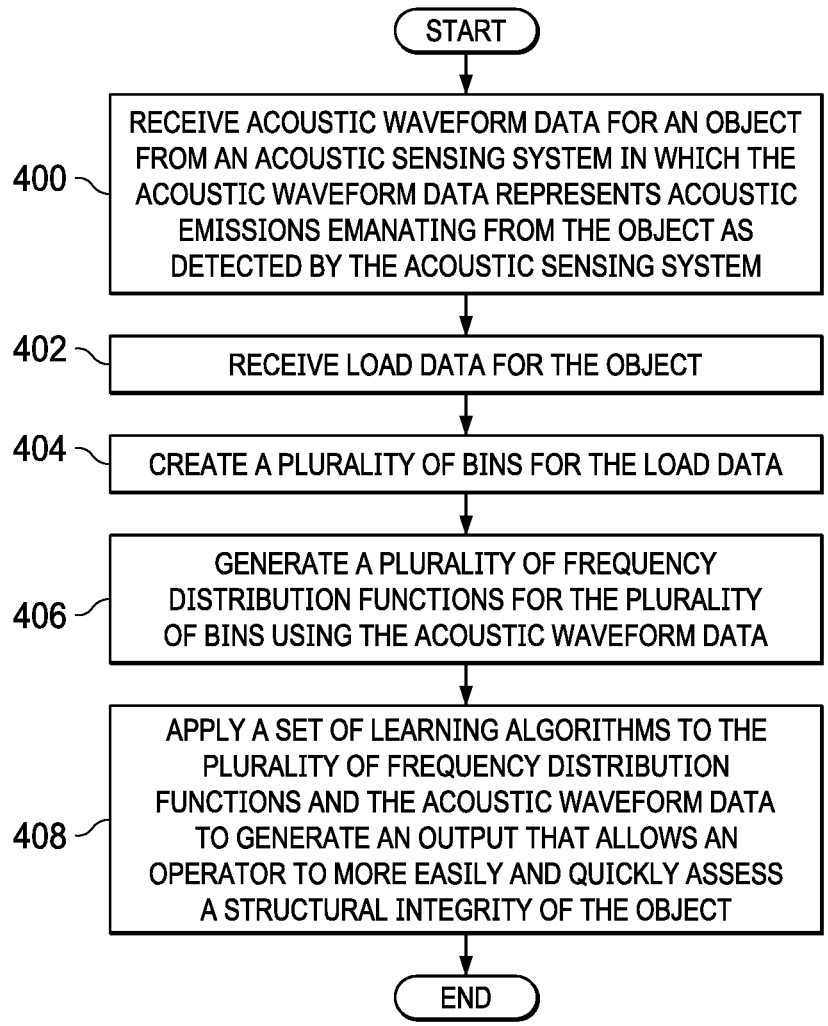
FIG. 4 is an illustration of a process for analyzing an object using acoustic emissions in the form of a flowchart in accordance with an illustrative embodiment.

With reference now to FIG. 4, an illustration of a process for analyzing an object using acoustic emissions is depicted in the form of a flowchart in accordance with an illustrative embodiment. The process illustrated in FIG. 4 may be implemented by analyzer module 214 described in FIG. 2.

The process may begin by receiving acoustic waveform data for an object from an acoustic sensing system in which the acoustic waveform data represents acoustic emissions emanating from the object as detected by the acoustic sensing system (operation 400). Next, load data for the object is received (operation 402). Thereafter, a plurality of bins is created for the load data (operation 404).

In operation 404, depending on the implementation, the plurality of bins may be a plurality of time bins or a plurality of load bins. A plurality of frequency distribution functions is then generated for the plurality of bins using the acoustic waveform data (operation 406). In operation 406, a frequency distribution function is generated for each bin in the plurality of bins. In some illustrative examples, the plurality of frequency distribution functions take the form of a plurality of frequency histograms.

Thereafter, a set of learning algorithms is applied to the plurality of frequency distribution functions and the acoustic waveform data to generate an output that allows an operator to more easily and quickly assess a structural integrity of the object (operation 408), with the process terminating thereafter. The process described in FIG. 4 may reduce the overall time, effort, and computer-based processing resources that are needed to accurately assess the structural integrity of the object when the object is subject to multiple modes of structural change occurring simultaneously.

Figure 5:
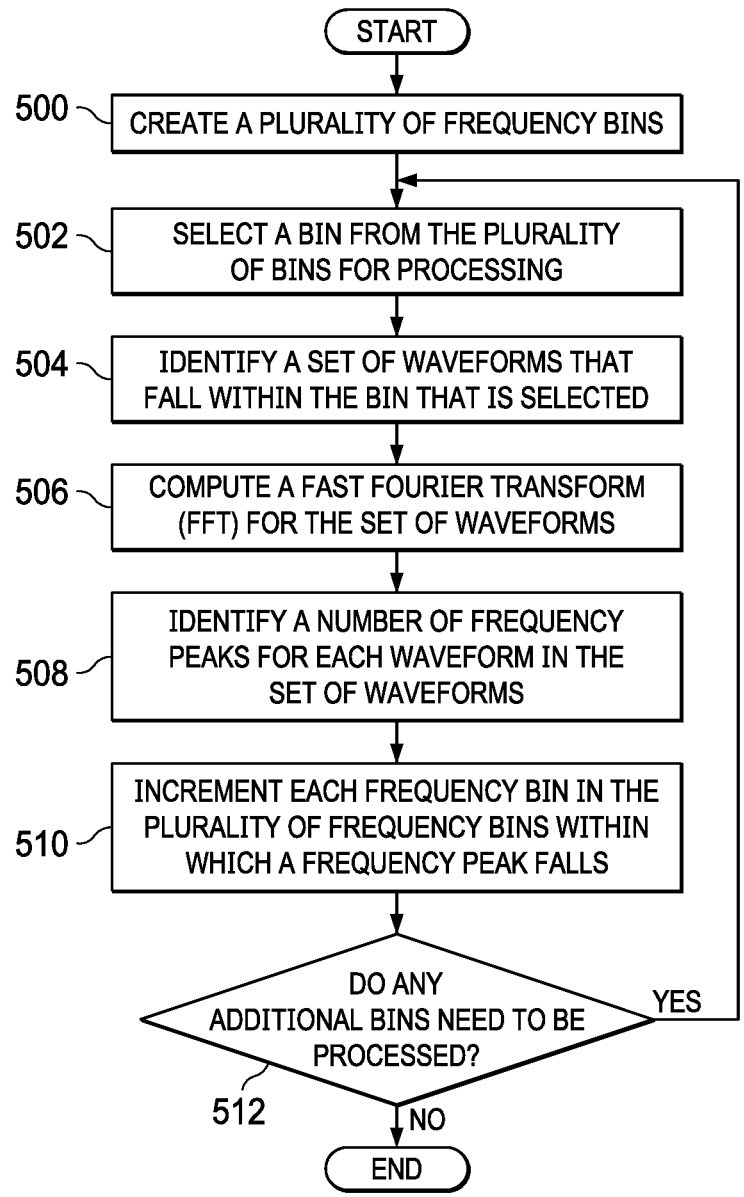
FIG. 5 is an illustration of a process for generating a plurality of frequency distribution functions in the form of a flowchart in accordance with an illustrative embodiment.

With reference now to FIG. 5, an illustration of a process for generating a plurality of frequency distribution functions is depicted in the form of a flowchart in accordance with an illustrative embodiment. The process illustrated in FIG. 5 may be implemented by analyzer module 214 described in FIG. 2. This process may be used to implement operation 406 in FIG. 4.

The process begins by creating a plurality of frequency bins (operation 500). In operation 500, each bin in the plurality of frequency bins may have a defined bin width. The bin widths of plurality of frequency bins may be the same or may be different. In one illustrative example, operation 500 is performed by dividing a selected frequency range into the plurality of frequency bins based on a defined frequency interval.

Thereafter, a bin is selected from the plurality of bins for processing (operation 502). In operation 502, the plurality of bins may be, for example, the plurality of bins created in operation 404 in FIG. 4.

Next, a set of waveforms that fall within the bin that is selected is identified (operation 504). A Fast Fourier Transform (FFT) is computed for the set of waveforms (operation 506). A number of frequency peaks is identified for each waveform in the set of waveforms (operation 508). Each frequency bin in the plurality of frequency bins within which a frequency peak falls is incremented (operation 510). In this manner, a frequency distribution function is created for the selected bin. Operation 510 is one example of how the plurality of frequency bins may be updated based on the Fast Fourier Transform computed in operation 506 and the number of frequency peaks identified for each waveform in the set of waveforms identified in operation 508.

A determination is then made as to whether any additional bins need to be processed (operation 512). If no additional bins need to be processed, the process terminates. Otherwise, the process returns to operation 502 described above.

The process described in FIG. 5 results in the generation of a plurality of frequency distribution functions for the plurality of bins.

Figure 6:
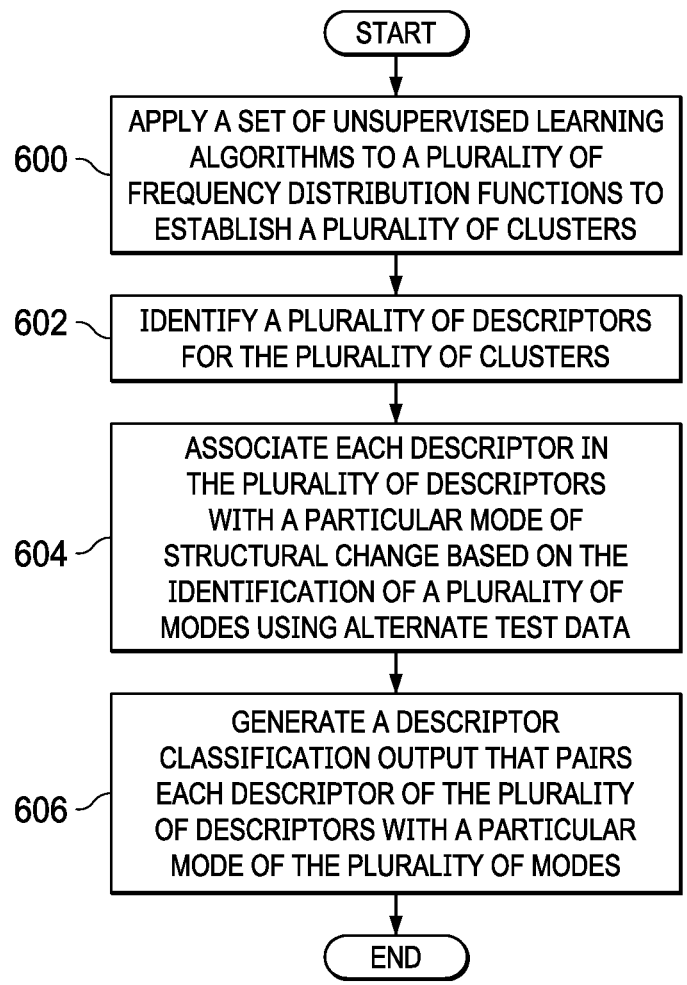
FIG. 6 is an illustration of one process, in the form of a flowchart, for applying a set of learning algorithms to a plurality of frequency distribution functions to generate an output in accordance with an illustrative embodiment.

With reference now to FIG. 6, an illustration of one process for applying a set of learning algorithms to a plurality of frequency distribution functions to generate an output is depicted in the form of a flowchart in accordance with an illustrative embodiment. The process illustrated in FIG. 6 may be implemented by analyzer module 214 in FIG. 2 and may be one example of how operation 408 in FIG. 4 may be implemented.

The process may begin by applying a set of unsupervised learning algorithms to a plurality of frequency distribution functions to establish a plurality of clusters (operation 600). In operation 600, the plurality of frequency distribution functions are grouped into clusters based on the unsupervised learning algorithms.

Next, a plurality of descriptors is identified for the plurality of clusters (operation 602). In operation 602, a descriptor is identified for each cluster. The descriptor is a representative frequency distribution function for the cluster. The descriptor for a particular cluster may be, for example, without limitation, a centroid frequency distribution function or a mean frequency distribution function for that cluster.

Thereafter, each descriptor in the plurality of descriptors is associated with a particular mode of structural change based on the identification of a plurality of modes using alternate test data (operation 604). In operation 604, the alternate test data may be, for example, x-ray data. Further, the plurality of modes may include, for example, without limitation, fiber breakage, splitting, split extension, delamination, crack formation, crack extension, or some other mode of structural change.

A descriptor classification output that pairs each descriptor of the plurality of descriptors with a particular mode of the plurality of modes is generated (operation 606), with the process terminating thereafter. This descriptor classification output may then be used to perform evaluation of the structural integrity of other objects.

Figure 7:
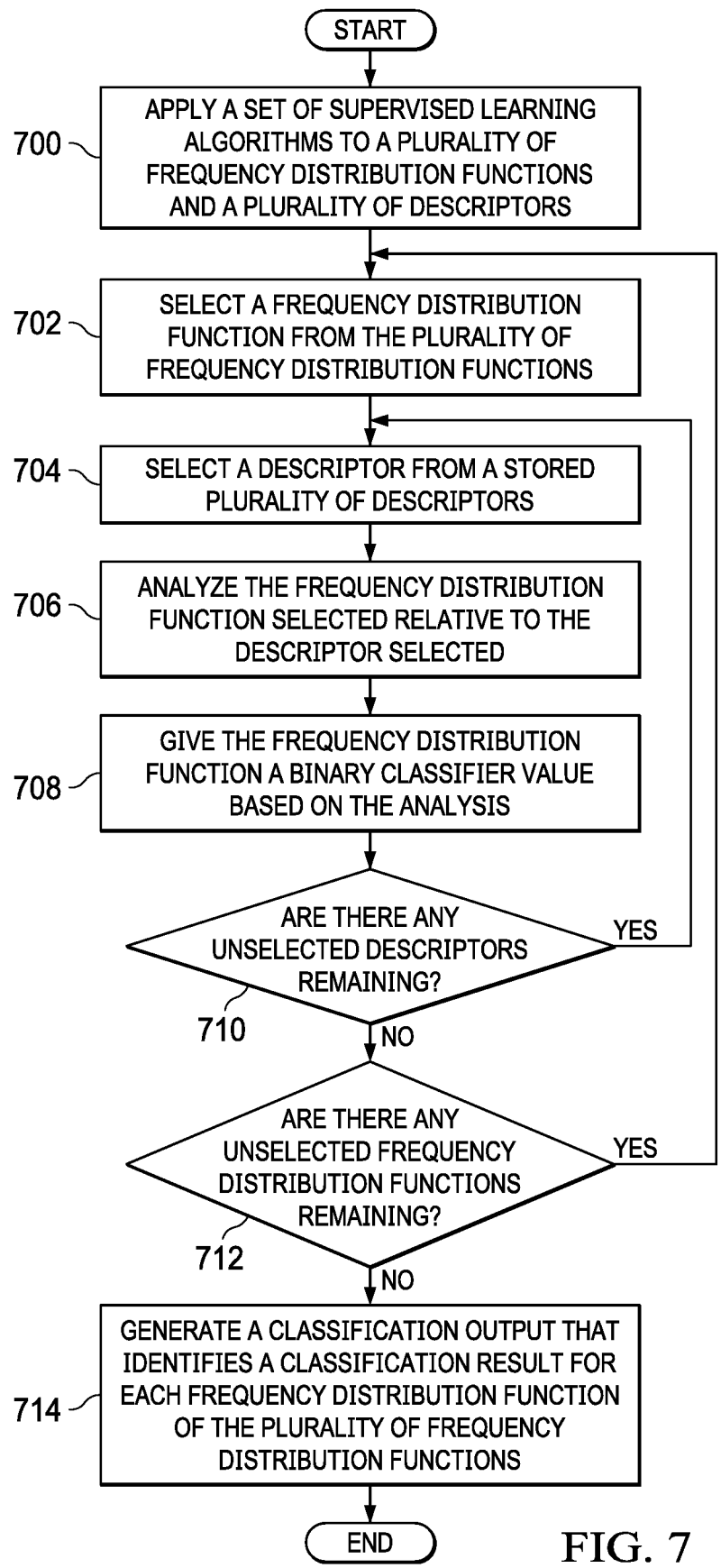
FIG. 7 is an illustration of another process, in the form of a flowchart, for applying a set of learning algorithms to a plurality of frequency distribution functions to generate an output in accordance with an illustrative embodiment.

With reference now to FIG. 7, an illustration of another process for applying a set of learning algorithms to a plurality of frequency distribution functions to generate an output is depicted in the form of a flowchart in accordance with an illustrative embodiment. The process illustrated in FIG. 7 may be implemented by analyzer module 214 in FIG. 2 and may be another example of how operation 408 in FIG. 4 may be implemented.

The process may begin by applying a set of supervised learning algorithms to a plurality of frequency distribution functions and a plurality of descriptors (operation 700). A frequency distribution function is selected from the plurality of frequency distribution functions (operation 702). Each frequency distribution function of the plurality of frequency distribution functions represents a set of waveforms that fall within a particular time bin or load bin based on load data.

Next, a descriptor is selected from a stored plurality of descriptors (operation 704). In operation 704, the stored plurality of descriptors may be previously identified for previously generated acoustic waveform data in a manner similar to the process described in FIG. 6. Each descriptor in the stored plurality of descriptors corresponds to a different mode of structural change.

Thereafter, the frequency distribution function selected is analyzed relative to the descriptor selected (operation 706). For example, in operation 706, the frequency distribution function may be compared to the descriptor, which may be a representative frequency distribution function for a cluster.

Next, the frequency distribution function is given a binary classifier value based on the analysis (operation 708). In operation 708, the binary classifier value may be either a first value or a second value. For example, the first value may indicate that the frequency distribution function does match the descriptor within selected tolerances, while the second value may indicate that the frequency distribution function does not match the descriptor within selected tolerances. In some cases, the first value and the second value may be referred to as a positive classification value and a negative classification value, respectively.

Thereafter, a determination is made as to whether any unselected descriptors remain (operation 710). If any unselected descriptors remain, the process returns to operation 704 described above. Otherwise, a determination is made as to whether any unselected frequency distribution functions remain (operation 712). If any unselected frequency distribution functions remain, the process returns to operation 702 described above.

Otherwise, the process generates a classification output that identifies a classification result for each frequency distribution function of the plurality of frequency distribution functions (operation 714), with the process terminating thereafter. In operation 714, the classification result for a particular frequency distribution function identifies whether that frequency distribution function represents zero, one, two, three, four, five, or some other number of modes of structural change.

Figure 8:
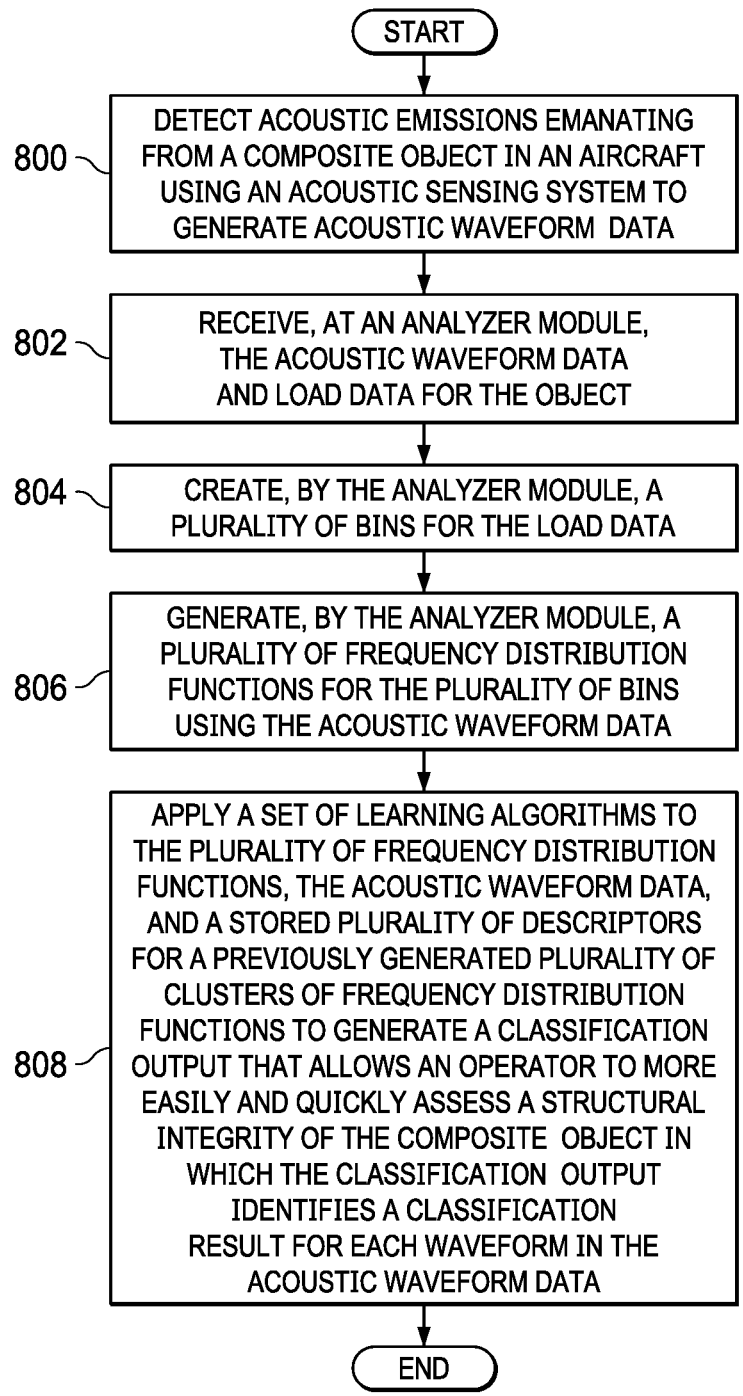
FIG. 8 is an illustration of a process for analyzing a composite object in an aircraft using acoustic emissions in the form of a flowchart in accordance with an illustrative embodiment.

With reference now to FIG. 8, an illustration of a process for analyzing a composite object in an aircraft using acoustic emissions is depicted in the form of a flowchart in accordance with an illustrative embodiment. The process illustrated in FIG. 8 may be implemented using acoustic sensing system 204 and analyzer module 214 described in FIG. 2.

The process may begin by detecting acoustic emissions emanating from a composite object in an aircraft using an acoustic sensing system to generate acoustic waveform data (800). Next, the acoustic waveform data and load data for the object is received at an analyzer module (802).

Thereafter, a plurality of bins is created, by the analyzer module, for the load data (operation 804). In operation 804, depending on the implementation, the plurality of bins may be a plurality of time bins or a plurality of load bins.

A plurality of frequency distribution functions is then generated, by the analyzer module, for the plurality of bins using the acoustic waveform data (operation 806). In operation 806, a frequency distribution function is generated for each bin in the plurality of bins. In some illustrative examples, the plurality of frequency distribution functions take the form of a plurality of frequency histograms.

Thereafter, a set of learning algorithms is applied to the plurality of frequency distribution functions, the acoustic waveform data, and a stored plurality of descriptors for a previously generated plurality of clusters of frequency distribution functions to generate a classification output that allows an operator to more easily and quickly assess a structural integrity of the composite object in which the classification output identifies a classification result for each waveform in the acoustic waveform data (operation 808), with the process terminating thereafter. In operation 808, the classification result may identify a particular waveform as representing zero, one, two, three, four, or some other number of modes of structural change.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 9:
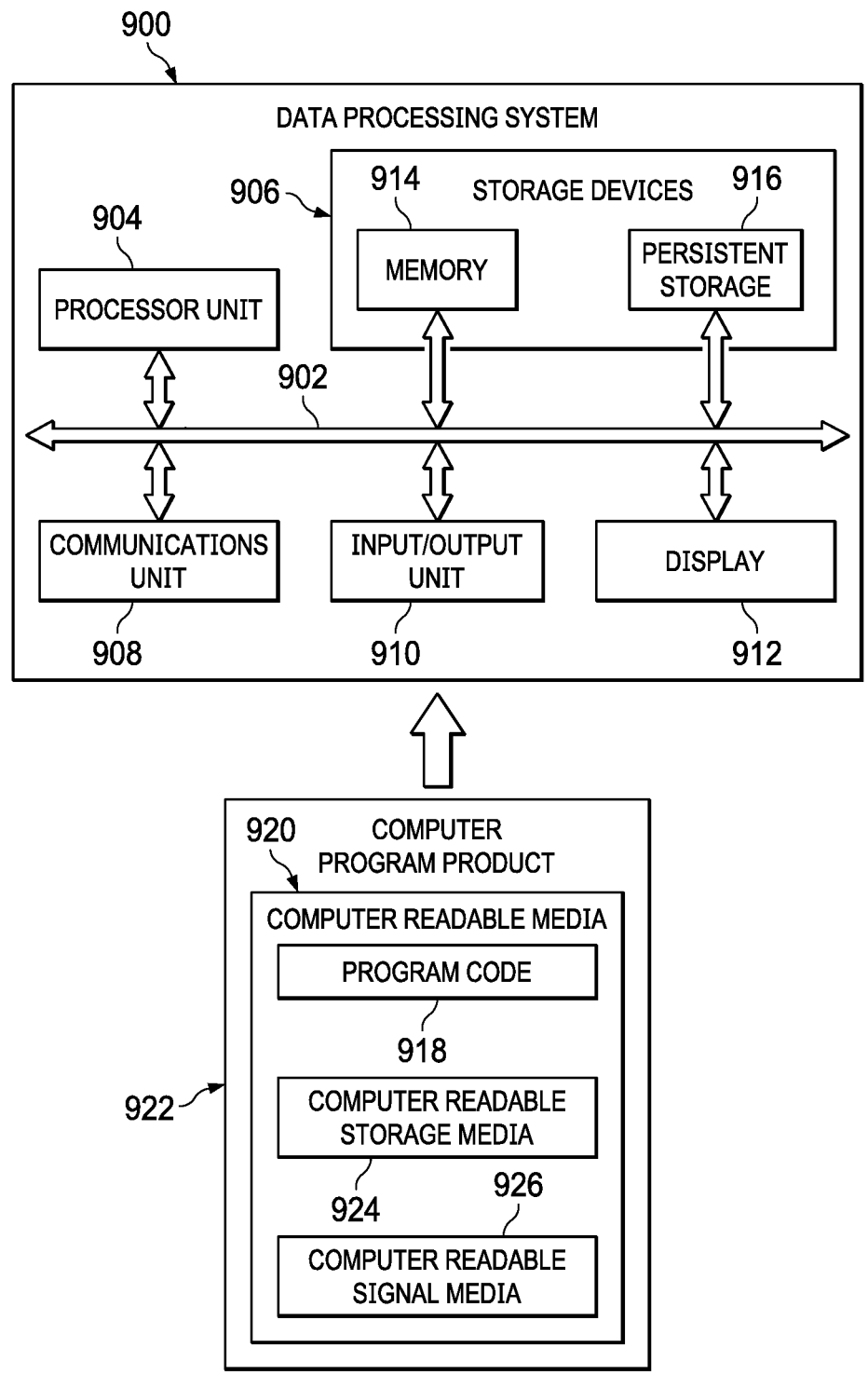
FIG. 9 is an illustration of a data processing system in the form of a block diagram in accordance with an illustrative embodiment.

Turning now to FIG. 9, an illustration of a data processing system in the form of a block diagram is depicted in accordance with an illustrative embodiment. Data processing system 900 may be used to implement analyzer module 214, computer system 216, or both in FIG. 2. As depicted, data processing system 900 includes communications framework 902, which provides communications between processor unit 904, storage devices 906, communications unit 908, input/output unit 910, and display 912. In some cases, communications framework 902 may be implemented as a bus system.

Processor unit 904 is configured to execute instructions for software to perform a number of operations. Processor unit 904 may comprise a number of processors, a multiprocessor core, and/or some other type of processor, depending on the implementation. In some cases, processor unit 904 may take the form of a hardware unit, such as a circuit system, an application specific integrated circuit (ASIC), a programmable logic device, or some other suitable type of hardware unit.

Instructions for the operating system, applications, and/or programs run by processor unit 904 may be located in storage devices 906. Storage devices 906 may be in communication with processor unit 904 through communications framework 902. As used herein, a storage device, also referred to as a computer readable storage device, is any piece of hardware capable of storing information on a temporary and/or permanent basis. This information may include, but is not limited to, data, program code, and/or other information.

Memory 914 and persistent storage 916 are examples of storage devices 906. Memory 914 may take the form of, for example, a random access memory or some type of volatile or non-volatile storage device. Persistent storage 916 may comprise any number of components or devices. For example, persistent storage 916 may comprise a hard drive, a flash memory, a rewritable optical disk, a rewritable magnetic tape, or some combination of the above. The media used by persistent storage 916 may or may not be removable.

Communications unit 908 allows data processing system 900 to communicate with other data processing systems and/or devices. Communications unit 908 may provide communications using physical and/or wireless communications links.

Input/output unit 910 allows input to be received from and output to be sent to other devices connected to data processing system 900. For example, input/output unit 910 may allow user input to be received through a keyboard, a mouse, and/or some other type of input device. As another example, input/output unit 910 may allow output to be sent to a printer connected to data processing system 900.

Display 912 is configured to display information to a user. Display 912 may comprise, for example, without limitation, a monitor, a touch screen, a laser display, a holographic display, a virtual display device, and/or some other type of display device.

In this illustrative example, the processes of the different illustrative embodiments may be performed by processor unit 904 using computer-implemented instructions. These instructions may be referred to as program code, computer usable program code, or computer readable program code and may be read and executed by one or more processors in processor unit 904.

In these examples, program code 918 is located in a functional form on computer readable media 920, which is selectively removable, and may be loaded onto or transferred to data processing system 900 for execution by processor unit 904. Program code 918 and computer readable media 920 together form computer program product 922. In this illustrative example, computer readable media 920 may be computer readable storage media 924 or computer readable signal media 926.

Computer readable storage media 924 is a physical or tangible storage device used to store program code 918 rather than a medium that propagates or transmits program code 918. Computer readable storage media 924 may be, for example, without limitation, an optical or magnetic disk or a persistent storage device that is connected to data processing system 900.

Alternatively, program code 918 may be transferred to data processing system 900 using computer readable signal media 926. Computer readable signal media 926 may be, for example, a propagated data signal containing program code 918. This data signal may be an electromagnetic signal, an optical signal, and/or some other type of signal that can be transmitted over physical and/or wireless communications links.

The illustration of data processing system 900 in FIG. 9 is not meant to provide architectural limitations to the manner in which the illustrative embodiments may be implemented. The different illustrative embodiments may be implemented in a data processing system that includes components in addition to or in place of those illustrated for data processing system 900. Further, components shown in FIG. 9 may be varied from the illustrative examples shown.

Figure 10:
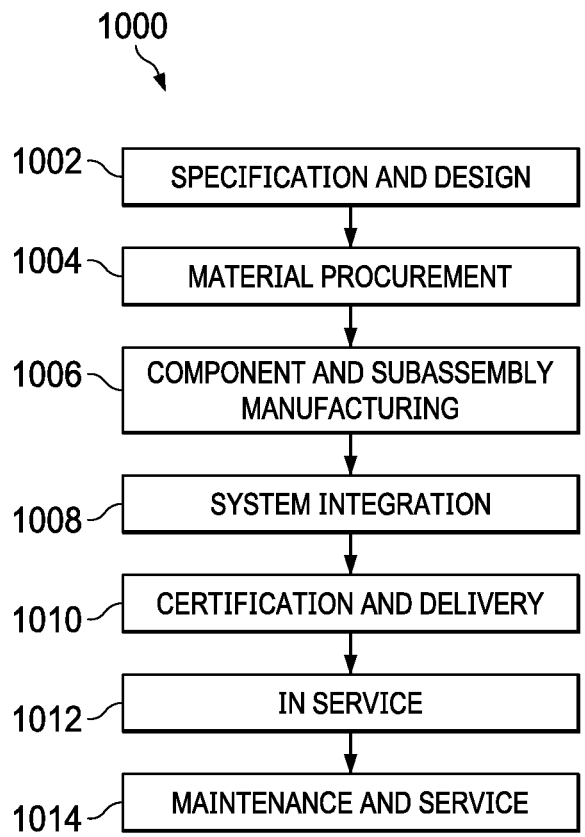
FIG. 10 is an illustration of an aircraft manufacturing and service method in the form of a block diagram in accordance with an illustrative embodiment.
Figure 11:
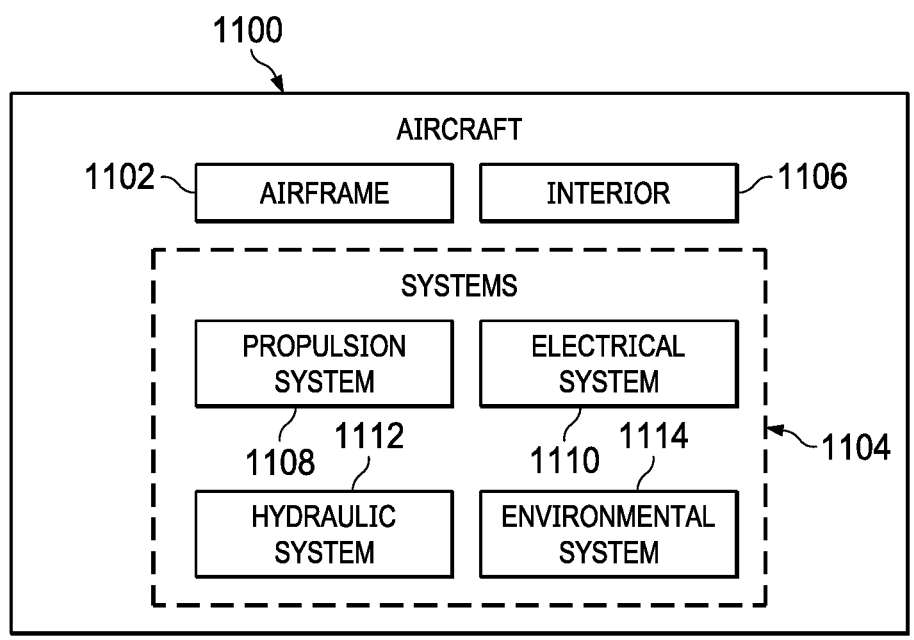
FIG. 11 is illustration of an aircraft in the form of a block diagram in accordance with an illustrative embodiment.

Illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in the form of a block diagram in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in which an illustrative embodiment may be implemented. In this example, aircraft 1100 is produced by aircraft manufacturing and service method 1000 in FIG. 10 and may include airframe 1102 with systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. In particular, acoustic sensing system 204 and analyzer module 214 from FIG. 2 may be used during any one of the stages of aircraft manufacturing and service method 1000.

For example, without limitation, acoustic sensing system 204 from FIG. 2 may be used to detect acoustic emissions from various parts in aircraft 1100 during at least one of component and subassembly manufacturing 1006, system integration 1008, in service 1012, routine maintenance and service 1014, or some other stage of aircraft manufacturing and service method 1000. Still further, analyzer module 214 from FIG. 2 may be used to analyze detected acoustic emissions during at least one of component and subassembly manufacturing 1006, system integration 1008, in service 1012, routine maintenance and service 1014, or some other stage of aircraft manufacturing and service method 1000.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012 and/or during maintenance and service 1014 in FIG. 10. The use of a number of the different illustrative embodiments may substantially expedite the assembly of and/or reduce the cost of aircraft 1100.

An apparatus comprises an acoustic sensing system and an analyzer module. The acoustic sensing system is positioned relative to an object. The acoustic sensing system detects acoustic emissions and generates acoustic waveform data for the acoustic emissions detected. The analyzer module is implemented in a computer system. The analyzer module receives load data and the acoustic waveform data for the object, creates a plurality of bins for the load data, generates a plurality of frequency distribution functions for the plurality of bins using the acoustic waveform data, and applies a set of learning algorithms to the plurality of frequency distribution functions and the acoustic waveform data to generate an output that allows an operator to more easily and quickly assess a structural integrity of the object.

In some illustrative examples, an acoustic sensor positioned in contact with the object. In some illustrative examples, the set of learning algorithms includes either a set of unsupervised learning algorithms or a set of supervised learning algorithms. In some illustrative examples, the load data is either retrieved from a database or received from a load sensing system that measures a loading of the object as the acoustic waveform data is generated.

In some illustrative examples, the plurality of bins have a plurality of bin widths and wherein a bin width in the plurality of bin widths is either a time interval or a load interval. In some illustrative examples, each frequency distribution function in the plurality of frequency distribution functions has a plurality of bin widths in which each bin width of the plurality of bin widths is a defined frequency interval. In some illustrative examples, each frequency distribution function in the plurality of frequency distribution functions comprises a plurality of frequency bins and wherein a frequency bin in the plurality of frequency bins includes either a count of a number of frequency peaks that fall within the frequency bin or an accumulation of energy at the frequency bin computed using the acoustic waveform data.

In some illustrative examples, the output identifies a plurality of clusters of the plurality of frequency distribution functions. In these illustrative examples, the plurality of clusters comprises: a first cluster representing a first mode of structural change; a second cluster representing a second mode of structural change; a third cluster representing a third mode of structural change; and a fourth cluster representing a fourth mode of structural change.

In some illustrative examples, the analyzer module applies the set of learning algorithms to the plurality of frequency distribution functions to establish a plurality of clusters and to identify a plurality of descriptors for the plurality of clusters. In some of these illustrative examples, the plurality of clusters is analyzed with alternate test data to associate each descriptor in the plurality of descriptors with a different mode of structural change and wherein the alternate test data is selected from one of x-ray imaging data, ultrasound imaging data, infrared imaging data, and modeling data. In some of these illustrative examples, the analyzer module generates a descriptor classification output that associates a mode of structural change with the each descriptor in the plurality of descriptors and wherein the descriptor classification output is stored in a database for future use in evaluating a structural integrity of a part during at least one stage in a lifecycle of the part.

A method is provided for analyzing an object using acoustic waves. Load data is received for the object. Acoustic waveform data is received for the object from an acoustic sensing system. The acoustic waveform data represents acoustic emissions emanating from the object and is detected using the acoustic sensing system. A plurality of bins is created for the load data. A plurality of frequency distribution functions is generated for the plurality of bins using the acoustic waveform data. A set of learning algorithms is applied to the plurality of frequency distribution functions and the acoustic waveform data to generate an output that allows an operator to more easily and quickly assess a structural integrity of the object. In some illustrative examples, the method further comprises detecting, by the acoustic sensing system, acoustic waves radiating from the object using at least one acoustic sensor to generate an acoustic emissions signal; and converting the acoustic emissions signal into the acoustic waveform data.

In some illustrative examples, creating the plurality of bins comprises: identifying a plurality of bin widths for the plurality of bins, wherein a bin width in the plurality of bin widths is either a defined time interval or a defined load interval; and identifying a set of waveforms in the acoustic waveform data that fall within each bin of the plurality of bins. In some of these illustrative examples, generating the plurality of frequency distribution functions comprises: dividing a selected frequency range into a plurality of frequency bins based on at least one defined frequency interval. In some of these illustrative examples, generating the plurality of frequency distribution functions further comprises: computing a Fast Fourier Transform for the set of waveforms that fall within a bin selected from the plurality of bins; and updating the plurality of frequency bins in a frequency distribution function for the bin based on the Fast Fourier Transform. In some of these illustrative examples, updating the plurality of frequency bins comprises: selecting a number of frequency peaks for each waveform in the set of waveforms; and incrementing a frequency bin in the plurality of frequency bins when a frequency peak in the number of frequency peaks has a frequency that falls within the frequency bin.

In some illustrative examples, applying the set of learning algorithms comprises: applying a set of unsupervised learning algorithms to the plurality of frequency distribution functions and the acoustic waveform data to establish a plurality of clusters; identifying a plurality of descriptors for the plurality of clusters; and generating a descriptor classification output that classifies each descriptor in the plurality of descriptors as representing a different mode of structural change based on a plurality of modes identified using alternate test data. In some illustrative examples, applying the set of learning algorithms comprises: applying a set of supervised learning algorithms to the plurality of frequency distribution functions, the acoustic waveform data, and a stored plurality of descriptors; and generating a classification result for each frequency distribution function of the plurality of frequency distribution functions.

A method is provided for monitoring a composite object in an aircraft during at least one stage in a lifecycle of the aircraft. Acoustics emissions radiating from the composite object are detected using an acoustic sensing system to generate acoustic waveform data. An analyzer module receives the acoustic waveform data and load data for the composite object. The analyzer module creates a plurality of bins for the load data. A set of waveforms in the acoustic waveform data falls within a corresponding bin in the plurality of bins. The analyzer module generates a plurality of frequency distribution functions for the plurality of bins using the acoustic waveform data. A set of supervised learning algorithms is applied to the plurality of frequency distribution functions, the acoustic waveform data, and a stored plurality of descriptors to generate a classification output that identifies a classification result for each frequency distribution function in the plurality of frequency distribution functions. The classification output allows an operator to more easily and quickly assess a structural integrity of the composite object.

In some illustrative examples, applying the set of supervised learning algorithms to the plurality of frequency distribution functions, the acoustic waveform data, and the stored plurality of descriptors to generate the classification output comprises: generating the classification result for a selected frequency distribution function in the plurality of frequency distribution functions by comparing the selected frequency distribution function to each of the stored plurality of descriptors, wherein the classification result identifies whether the selected frequency distribution function, and thereby a corresponding set of waveforms in the acoustic waveform data, represents zero or more modes of structural change.

Figure 12:
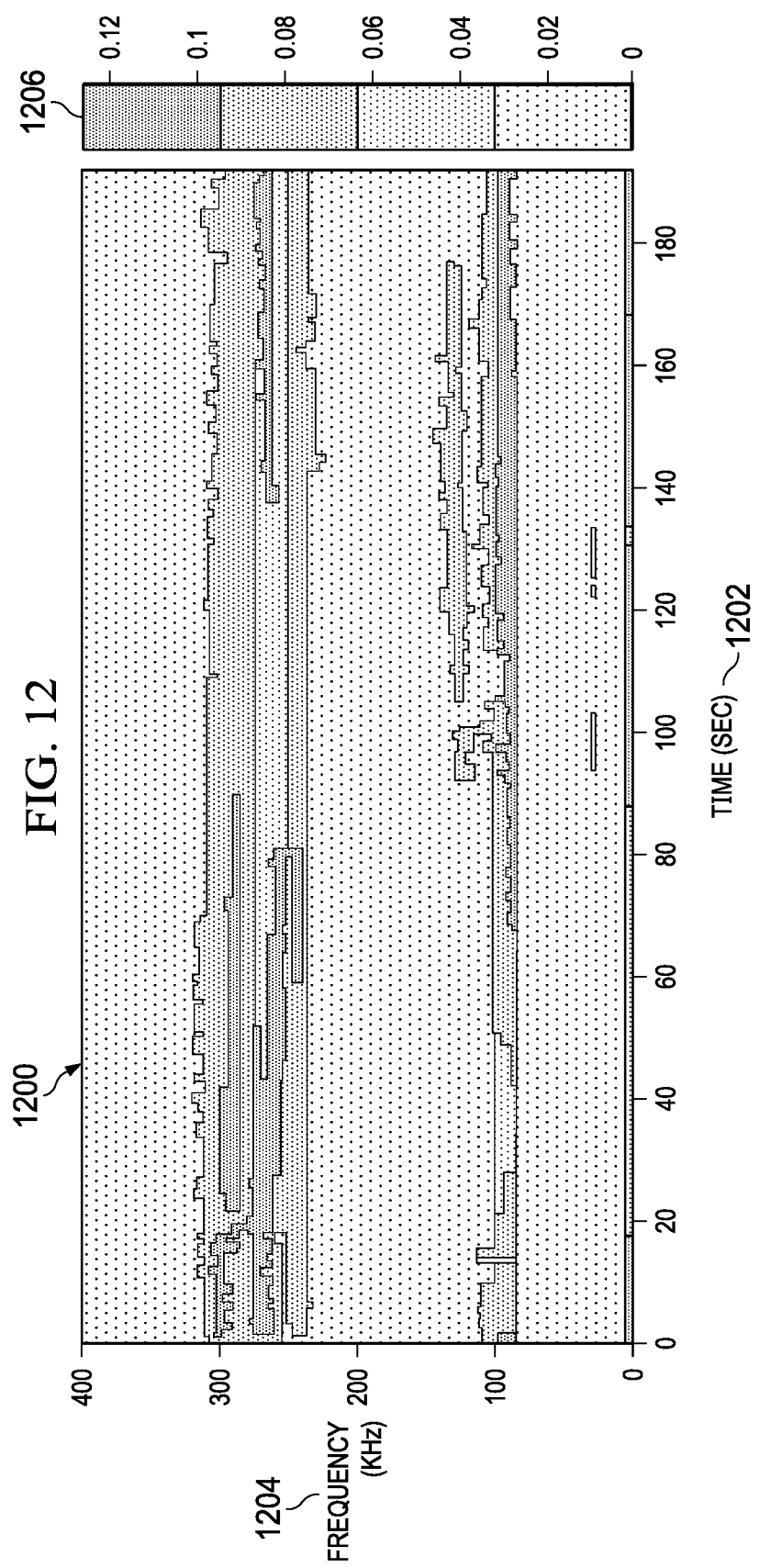
FIG. 12 is an illustration of a frequency distribution function time evolution image in accordance with an illustrative embodiment.

Turning now to FIG. 12, an illustration of a frequency distribution function time evolution image is depicted in accordance with an illustrative embodiment. Frequency distribution function time evolution image 1200 is an example of an image formed with a plurality of points of each of plurality of frequency distribution functions 228 of FIG. 2. As used herein, a "plurality" of items is more than one item. For example, a plurality of points is more than one point. When a plurality of points of each of plurality of frequency distribution functions 228 is used to form frequency distribution function time evolution image 1200, more than one point of each of plurality of frequency distribution functions 228 is used to form frequency distribution function time evolution image 1200. In some illustrative examples, frequency distribution function time evolution image 1200 is an example of an image formed with all data of each of plurality of frequency distribution functions 228 of FIG. 2.

Frequency distribution function time evolution image 1200 may be used to tune parameters used to create plurality of frequency distribution functions 228 of FIG. 2. Frequency distribution function time evolution image 1200 may be used to determine changes to an object or assess a structural integrity of the object, such as object 200 of FIG. 2.

Frequency distribution function time evolution image 1200 has x-axis 1202 and y-axis 1204. Y-axis 1204 is a frequency. As depicted, x-axis 1202 is time. In other illustrative examples, x-axis 1202 is load.

Legend 1206 identifies the correlation between amplitude and color for each pixel of frequency distribution function time evolution image 1200. Each column of frequency distribution function time evolution image 1200 contains the data of a single frequency distribution function.

In some illustrative examples, it is desirable to identify values for at least one of plurality of bin widths 226, plurality of frequency bins 235, a quantity of frequency peaks in frequency peaks 240 of FIG. 2, and a quantity of plurality of clusters 242 of FIG. 2. The illustration of object 200, acoustic sensing system 204, and analyzer module 214 in FIG. 2 is not meant to imply physical or architectural limitations to the manner in which an illustrative embodiment may be implemented. The different components shown in FIGS. 1-3 may be combined with components in FIGS. 12-16, used with components in FIGS. 12-16, or a combination of the two.

Figure 13:
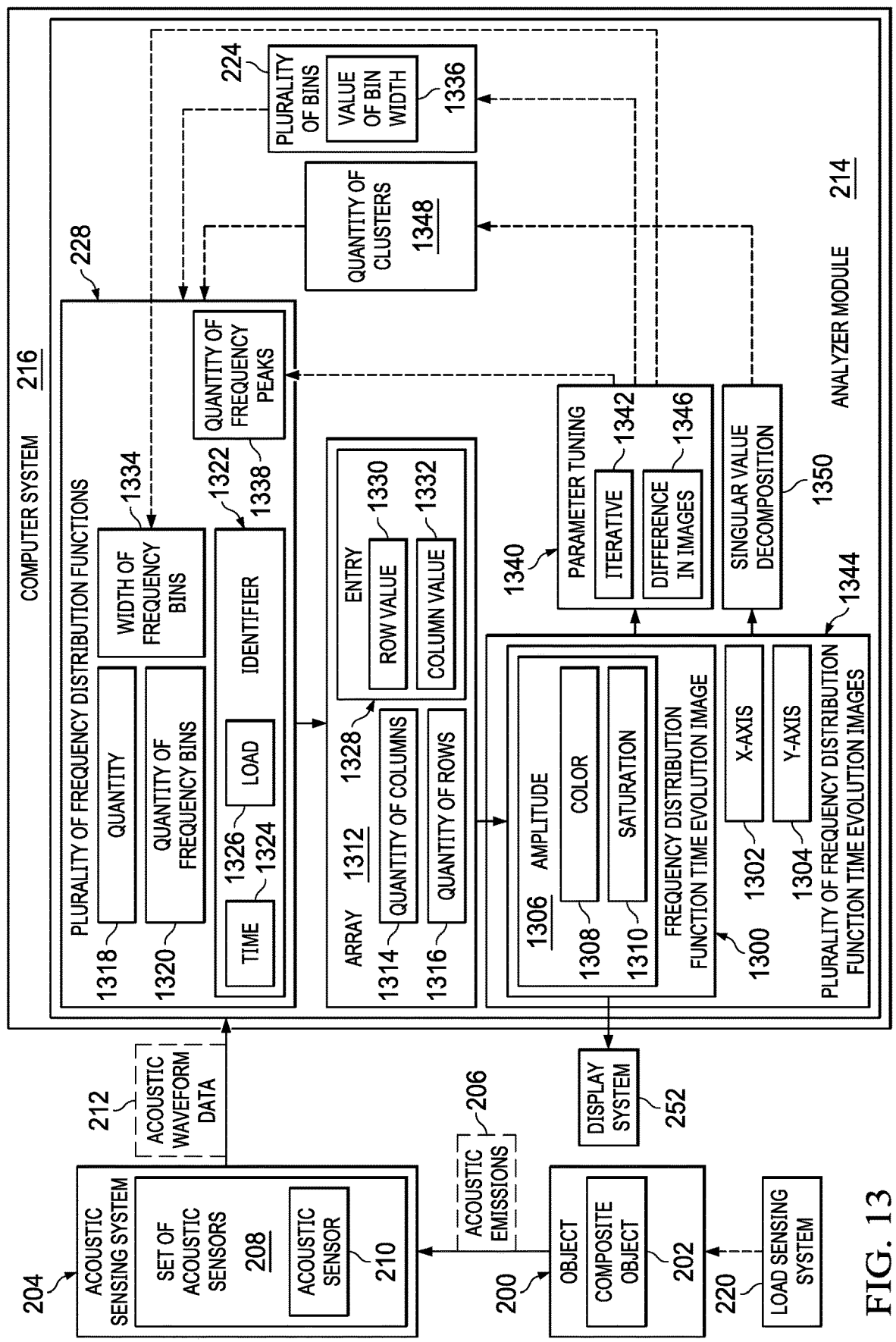
FIG. 13 is an illustration of an object, an acoustic sensing system, and an analyzer module in the form of a block diagram in accordance with an illustrative embodiment.

Turning now to FIG. 13, an illustration of an object, an acoustic sensing system, and an analyzer module in the form of a block diagram is depicted in accordance with an illustrative embodiment. FIG. 13 includes object 200, acoustic sensing system 204, and analyzer module 214 previously shown in FIG. 2. FIG. 13 also contains components used in forming or analyzing components of FIG. 2.

In some illustrative examples, analyzer module 214 generates frequency distribution function time evolution image 1300 using acoustic waveform data 212 for object 200. In some illustrative examples, frequency distribution function time evolution image 1300 is displayed on display system 252. When displayed, frequency distribution function time evolution image 1300 allows an operator to assess a structural integrity of object 200.

Data of each of plurality of frequency distribution functions 228 is contained in frequency distribution function time evolution image 1300. Frequency distribution function time evolution image 1200 of FIG. 12 is a physical implementation of frequency distribution function time evolution image 1300.

Frequency distribution function time evolution image 1300 has x-axis 1302 of either time or load. Frequency distribution function time evolution image 1300 has y-axis 1304 of frequency. Frequency distribution function time evolution image 1300 identifies amplitude 1306 using one of color 1308 or saturation 1310.

Frequency distribution function time evolution image 1300 is a display of array 1312. Array 1312 has quantity of columns 1314 and quantity of rows 1316. Array 1312 has quantity of columns 1314 equivalent to quantity 1318 of frequency distribution functions in plurality of frequency distribution functions 228. Array 1312 has quantity of rows 1316 equivalent to quantity of frequency bins 1320 in each frequency distribution function of plurality of frequency distribution functions 228. Each frequency distribution function of plurality of frequency distribution functions 228 has identifier 1322. Identifier 1322 is a unique range to a respective frequency distribution function of plurality of frequency distribution functions 228. This range may be expressed as either time 1324 or load 1326.

When identifier 1322 is time 1324, plurality of bin widths 226 of FIG. 2 is a plurality of time-based bin widths. In other words, each bin of plurality of bins 224 of FIG. 2 may correspond to a time interval. When identifier 1322 is load 1326, plurality of bin widths 226 of FIG. 2 is a plurality of load-based bin widths.

Array 1312 is filled such that a plurality of points of each of plurality of frequency distribution functions 228 is contained within array 1312. In some illustrative examples, array 1312 is filled such that all data of each of plurality of frequency distribution functions 228 is contained with array 1312. Array 1312 allows analyzer module 214 to identify structural changes in object 200 previously unidentifiable by an operator using frequency plots containing a single point extracted from each waveform of acoustic waveform data 212.

Each entry of array 1312 correlates to a sample of one of the respective frequency distribution functions of plurality of frequency distribution functions 228. Entry 1328 has row value 1330 and column value 1332. Row value 1330 indicates the row for entry 1328. Column value 1332 indicates the column for entry 1328. When row value 1330 is the xth row and column value 1332 is the yth column, entry 1328 contains the value of the yth frequency bin of the xth frequency distribution function.

Plurality of frequency distribution functions 228 is created using parameters including width of frequency bins 1334, value of bin width 1336, and quantity of frequency peaks 1338. In some illustrative examples, at least one of width of frequency bins 1334, value of bin width 1336, and quantity of frequency peaks 1338 is selected by an operator.

Each of width of frequency bins 1334, value of bin width 1336, and quantity of frequency peaks 1338 may be tuned using parameter tuning 1340. Parameter tuning 1340 is iterative 1342 and may be referred to as iterative parameter tuning.

In some illustrative examples, at least one of width of frequency bins 1334, value of bin width 1336, and quantity of frequency peaks 1338 is identified using parameter tuning 1340 and plurality of frequency distribution function time evolution images 1344 generated from acoustic waveform data 212. Parameter tuning 1340 generates plurality of frequency distribution function time evolution images 1344 for a plurality of values of a parameter of interest. Difference in images 1346 is determined between each successive pair of plurality of frequency distribution function time evolution images 1344. A quantity for the parameter of interest is selected from difference in images 1346.

In some illustrative examples, a quantity for a parameter of interest is selected from a range of operator provided values. For example, an operator may provide a range of values for each of width of frequency bins 1334, value of bin width 1336, and quantity of frequency peaks 1338 to receive parameter tuning 1340. Parameter tuning 1340 is performed by generating plurality of frequency distribution function time evolution images 1344 for every combination of values within the provided ranges for the parameters. When only a single parameter of interest receives parameter tuning 1340, plurality of frequency distribution function time evolution images 1344 is generated using each value in the respective range of values for the parameter of interest.

In some illustrative examples, two parameters of width of frequency bins 1334, value of bin width 1336, and quantity of frequency peaks 1338 are tuned using parameter tuning 1340. In these illustrative examples, the third parameter is kept at a constant value. After tuning the two parameters, the two values determined through parameter tuning 1340 are used to tune the last parameter using parameter tuning 1340.

Width of frequency bins 1334, value of bin width 1336, and quantity of frequency peaks 1338 may be tuned using parameter tuning 1340 in any desirable order. In some illustrative examples, the order for parameter tuning 1340 is influenced by the material forming object 200. In some illustrative examples, a desirable range for at least one of width of frequency bins 1334, value of bin width 1336, or quantity of frequency peaks 1338 is affected by the material of object 200. In some illustrative examples, the size of a range for at least one of width of frequency bins 1334, value of bin width 1336, or quantity of frequency peaks 1338 is affected by the material of object 200. For example, when object 200 is composite object 202, acoustic emissions have a frequency in the range of 100-1000 kHz. Due to the acoustic emissions frequency range of composite object 202, a range for width of frequency bins 1334 is limited. In some illustrative examples, when object 200 is composite object 202, width of frequency bins 1334 is tuned after tuning value of bin width 1336 and quantity of frequency peaks 1338 using parameter tuning 1340. In some of these illustrative examples, width of frequency bins 1334 is set at a value in the range of 20-50 kHz to initially tune value of bin width 1336 and quantity of frequency peaks 1338.

In some illustrative examples, a quantity for a parameter of interest is selected within a difference in terms of percentage at a steady state condition. For example, the steady state condition may be 5% difference between a pair of successive images. As another example, the steady state condition may be 13% difference between a pair of successive images. In some illustrative examples, a quantity for a parameter of interest is selected when the change is within 10% of a change of steady state. For example, if the steady state condition is 8% difference between a pair of successive images, a value for the parameter of interest may be selected when the difference value is between 18% and the steady state of 8%. As another example, if the steady state condition is 20% difference between a pair of successive images, a value for the parameter of interest may be selected when the difference value is between 30% and the steady state of 20%.

In some illustrative examples, analyzer module 214 selects quantity of clusters 1348. In some illustrative examples, analyzer module 214 identifies quantity of clusters 1348 using singular value decomposition 1350 of frequency distribution function time evolution image 1300. In some illustrative examples, determining quantity of clusters 1348 comprises selecting quantity of clusters 1348 from entries within a curved portion of a plot of the singular values from singular value decomposition 1350 on frequency distribution function time evolution image 1300.

Figure 14:
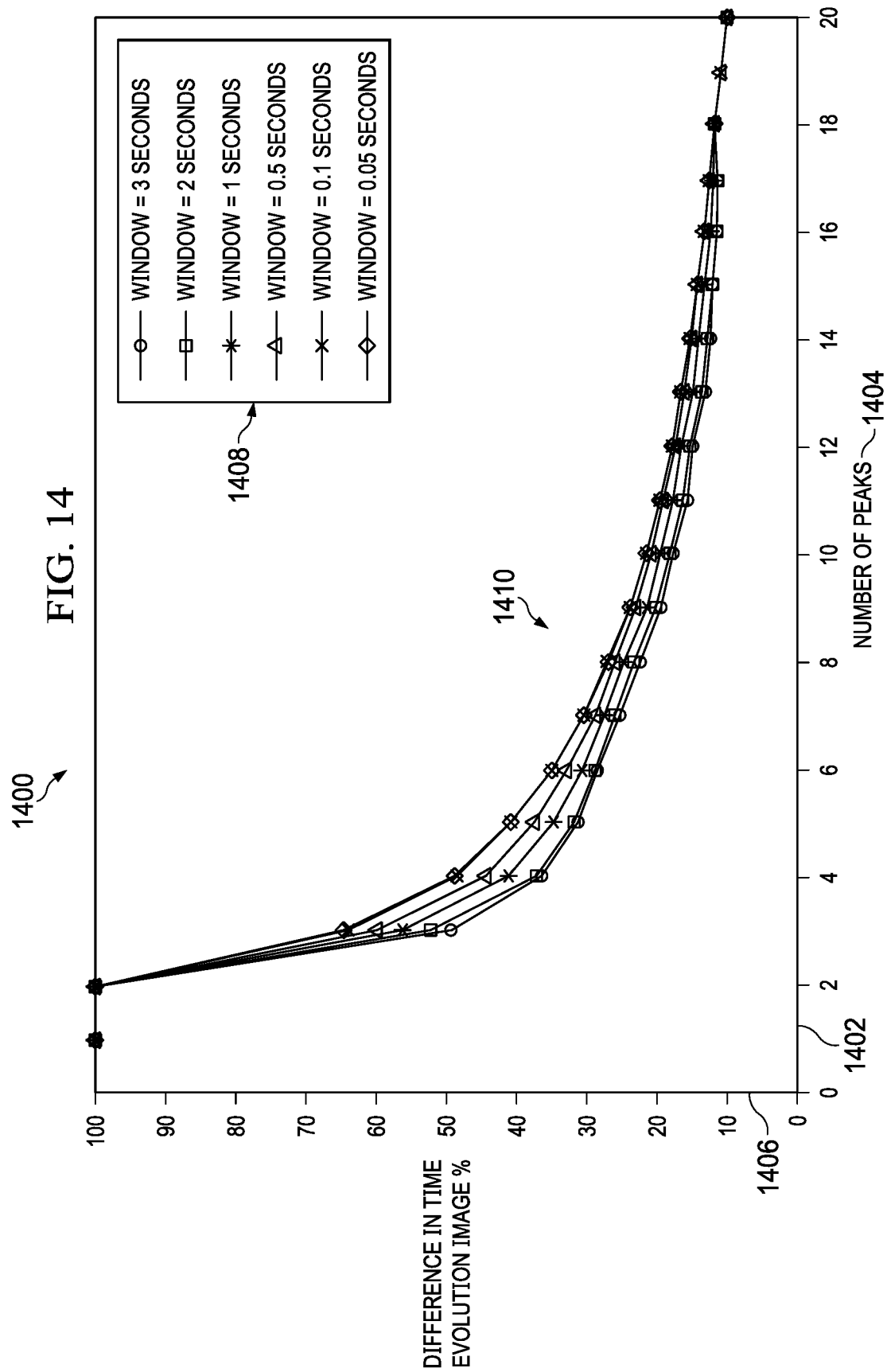
FIG. 14 is an illustration of a difference in change graph that may be used to tune parameters in accordance with an illustrative embodiment.

Turning now to FIG. 14, an illustration of a difference in change graph that may be used to tune parameters is depicted in accordance with an illustrative embodiment. Difference in change graph 1400 is a physical illustration of difference in images 1346 of FIG. 13. Difference in change graph 1400 is an example of a graph used in parameter tuning 1340 of FIG. 13. Any desirable parameter of width of frequency bins 1334, value of bin width 1336, or quantity of frequency peaks 1338 of FIG. 13 may be tuned using a difference in change graph, such as difference in change graph 1400.

As depicted, difference in change graph 1400 is a physical implementation of a graph that may be used to tune quantity of frequency peaks 1338 of FIG. 13. Difference in change graph 1400 has x-axis 1402 of quantity of peaks 1404. Difference in change graph 1400 has y-axis 1406 of difference in change between successive frequency distribution function time evolution images.

In difference in change graph 1400, legend 1408 shows the length of time window for testing. The length of time window is a width of the plurality of frequency bins, such as width of frequency bins 1334 of FIG. 13. The length of time window is a width of plurality of frequency bins 235 of FIG. 2. As depicted, each curve of curves 1410 reaches steady state around 10%. When the change is within 10% of change of steady state, the value for quantity of peaks 1404 may be selected. As depicted, each of curves 1410 reaches within 10% of change of steady state between 8 peaks and 10 peaks. A value for quantity of frequency peaks 1338 of FIG. 13 may desirably be in the range of 8 to 10 peaks. In other illustrative examples, other desirable quantities of peaks may be determined depending on the applicable difference in change graph.

In some illustrative examples, width of frequency bins 1334 of FIG. 13 may be decided from FIG. 14. In some illustrative examples, options for width of frequency bins 1334 of FIG. 13 may be eliminated using FIG. 14. For example, window=0.1 seconds and window=0.05 seconds may be eliminated from FIG. 14. Window=0.1 seconds and window=0.05 seconds are substantially on top of one another. If a plot of the difference as a function of frequency bin width is created, the difference would be at steady state by frequency bin size 0.05.

Figure 15:
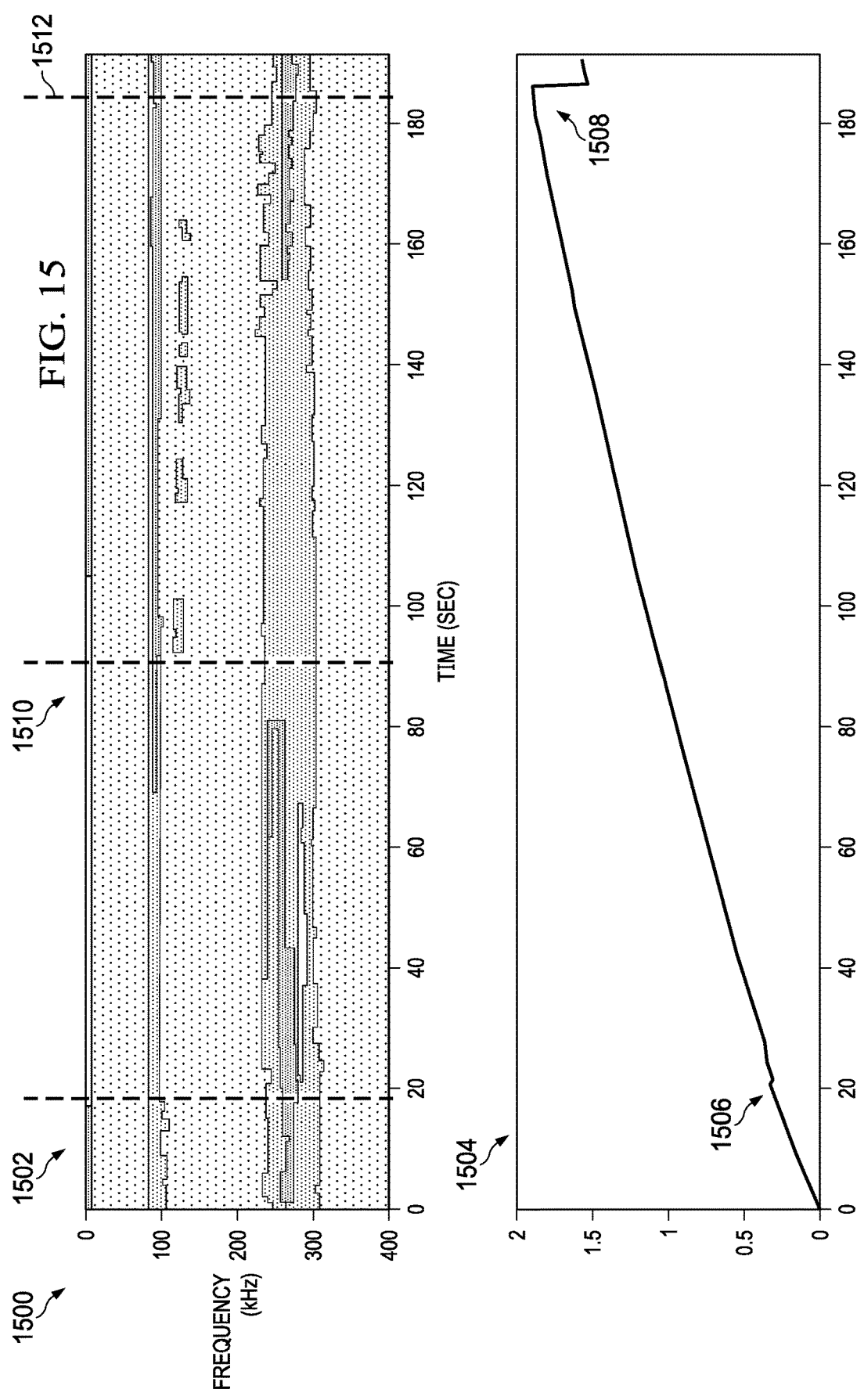
FIG. 15 is an illustration of a frequency distribution function time evolution image beside a normalized loading curve in accordance with an illustrative embodiment.

Turning now to FIG. 15, an illustration of a frequency distribution function time evolution image beside a normalized loading curve is depicted in accordance with an illustrative embodiment. View 1500 includes frequency distribution function time evolution image 1502 and normalized loading curve 1504. Normalized loading curve 1504 includes dip 1506 and dip 1508. Each of dip 1506 and dip 1508 indicates changes to the object being tested.

Normalized loading curve 1504 may be used to perform a validation step confirming that all instances of material changes in normalized loading curve 1504 are also present in frequency distribution function time evolution image 1502. Frequency distribution function time evolution image 1502 captures changes displayed in normalized loading curve 1504 and additional changes not detected by normalized loading curve 1504.

In some illustrative examples, clusters, such as plurality of clusters 242 of FIG. 2, may be selected by an operator based on at least one of normalized loading curve 1504 or frequency distribution function time evolution image 1502. In some illustrative examples, a quantity of clusters, such as quantity of clusters 1348 of FIG. 13. may be selected by an operator based on at least one of normalized loading curve 1504 or frequency distribution function time evolution image 1502.

As depicted, four clusters, clusters 1510, are separated by dashed lines 1512. As depicted, dashed lines 1512 extend through dip 1506 and dip 1508.

In some illustrative examples, a quantity of clusters, such as quantity of clusters 1348, may be selected automatically by an analyzer module, such as analyzer module 214 of FIGS. 2 and 13. When an analyzer module selects a quantity of clusters, the analyzer module performs calculations using data from frequency distribution function time evolution image 1502.

Figure 16:
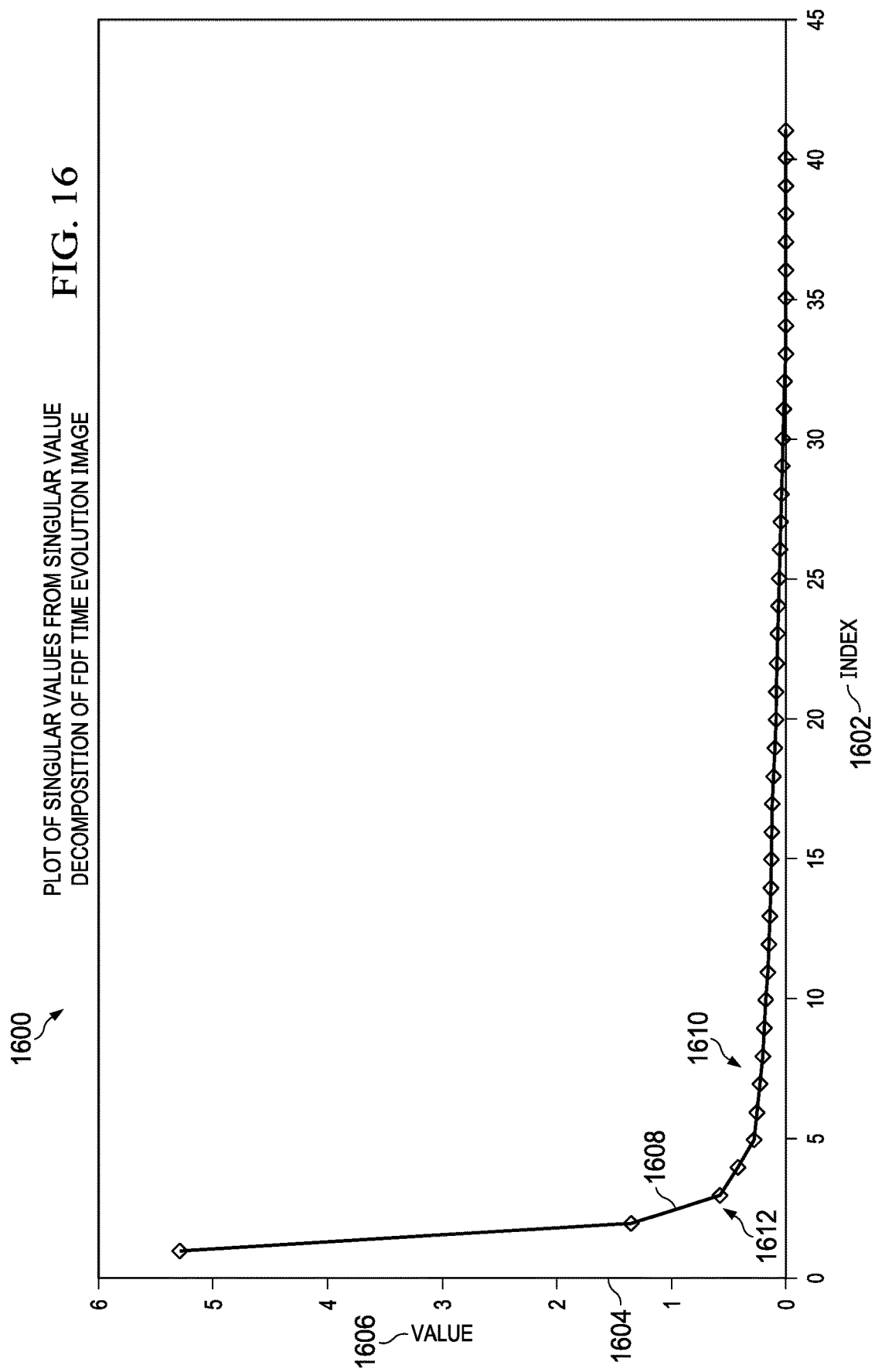
FIG. 16 is an illustration of a plot of singular values from singular value decomposition of a frequency distribution function time evolution image in accordance with an illustrative embodiment.

Turning now to FIG. 16, an illustration of a plot of singular values from singular value decomposition of a frequency distribution function time evolution image is depicted in accordance with an illustrative embodiment. In some illustrative examples, plot of singular values 1600 is a physical implementation of results of singular value decomposition 1350 of FIG. 13. Plot of singular values 1600 may be used to select quantity of clusters 1348 of FIG. 13. Analyzer module 214 of FIGS. 2 and 13 may perform calculations to create plot of singular values 1600 and determine quantity of clusters 1348. A quantity of clusters is selected after selecting each of width of frequency bins 1334, value of bin width 1336, and quantity of frequency peaks 1338.

Plot of singular values 1600 has x-axis 1602 and y-axis 1604. X-axis 1602 is a series of whole numerals for a quantity of clusters. Y-axis 1604 is singular values 1606 from singular value decomposition of frequency distribution function time evolution image 1502 of FIG. 15.

As depicted, line 1608 extends through plurality of points 1610. Line 1608 has curved portion 1612. In some illustrative examples, the quantity of clusters is selected from entries of plurality of points 1610 within curved portion 1612 of plot of singular values 1600.

Figure 17:
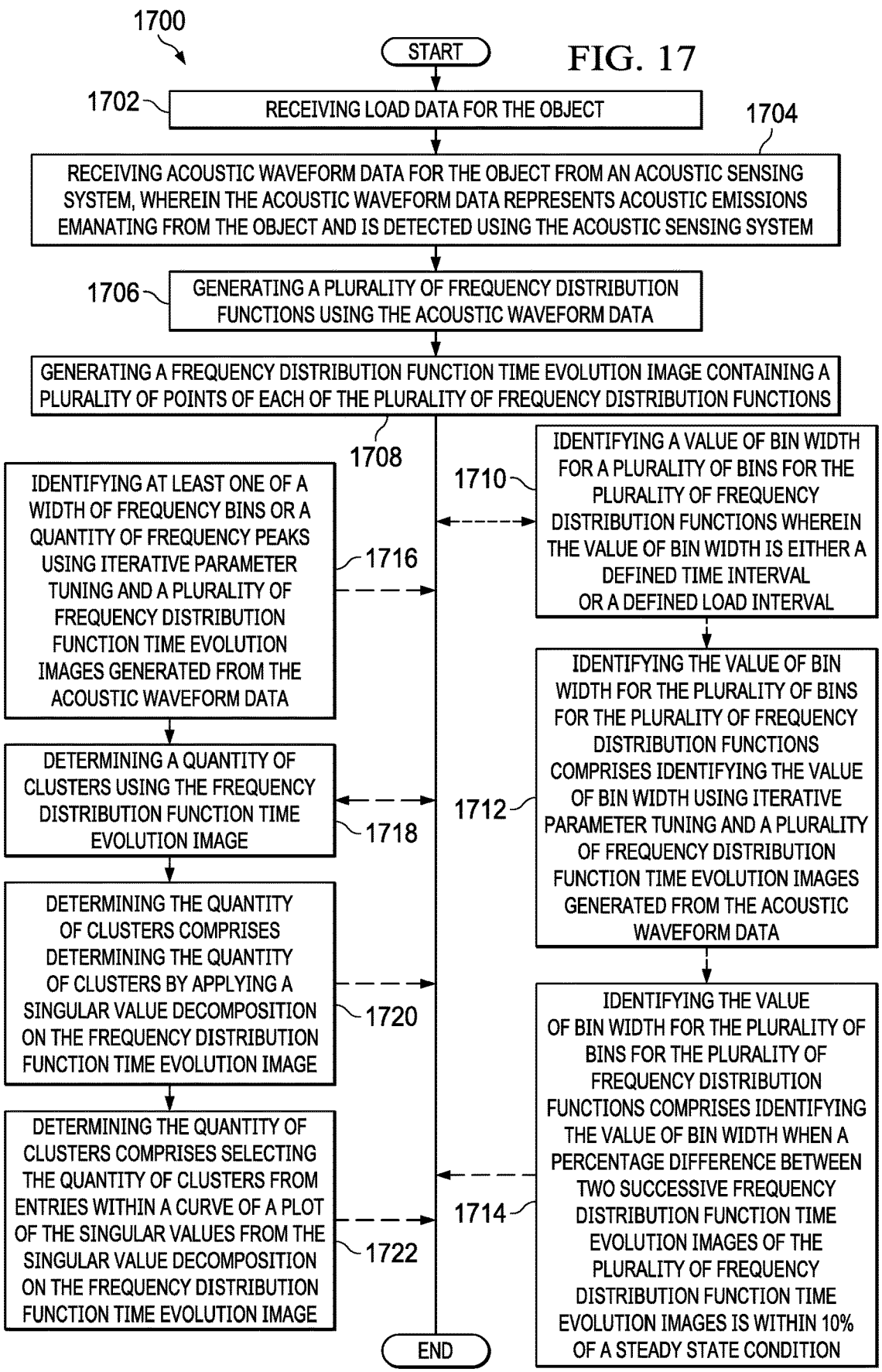
FIG. 17 is an illustration of a flowchart of a method for analyzing an object using acoustic waves in accordance with an illustrative embodiment.

Turning now to FIG. 17, an illustration of a flowchart of a method for analyzing an object using acoustic waves is depicted in accordance with an illustrative embodiment. Method 1700 may be implemented in test environment 100 of FIG. 1. Method 1700 may be implemented using acoustic sensing system 204 and analyzer module 214 of computer system 216 of FIGS. 2 and 13.

Method 1700 is a method for analyzing an object using acoustic waves. Method 1700 receives load data for the object (operation 1702). Method 1700 receives acoustic waveform data for the object from an acoustic sensing system, wherein the acoustic waveform data represents acoustic emissions emanating from the object and is detected using the acoustic sensing system (operation 1704). Method 1700 generates a plurality of frequency distribution functions using the acoustic waveform data (operation 1706). Method 1700 generates a frequency distribution function time evolution image containing a plurality of points of each of the plurality of frequency distribution functions (operation 1708). Afterwards, method 1700 terminates.

In some illustrative examples, method 1700 generates a frequency distribution function time evolution image containing all data of each of the plurality of frequency distribution functions. In some illustrative examples, the frequency distribution function time evolution image allows an operator to assess a structural integrity of the object. In some illustrative examples, the frequency distribution function time evolution image is used by an analyzer module to assess the structural integrity of the object. In some illustrative examples, the frequency distribution function time evolution image or the data contained in the frequency distribution function time evolution image allows the analyzer module to identify structural changes in the object previously unidentifiable by an operator using frequency plots containing a single point for each waveform of the acoustic waveform data.

In some illustrative examples, method 1700 identifies a value of bin width for a plurality of bins for the plurality of frequency distribution functions, wherein the value of bin width is either a defined time interval or a defined load interval (operation 1710). In some of these illustrative examples, identifying the value of bin width for the plurality of bins for the plurality of frequency distribution functions comprises identifying the value of bin width using iterative parameter tuning and a plurality of frequency distribution function time evolution images generated from the acoustic waveform data (operation 1712). In some of these illustrative examples, identifying the value of bin width for the plurality of bins for the plurality of frequency distribution functions comprises identifying the value of bin width when a percentage difference between two successive frequency distribution function time evolution images of the plurality of frequency distribution function time evolution images is within 10% of change of a steady state condition (operation 1714).

In some illustrative examples, method 1700 identifies at least one of a width of frequency bins or a quantity of frequency peaks using iterative parameter tuning and a plurality of frequency distribution function time evolution images generated from the acoustic waveform data (operation 1716).

In some illustrative examples, method 1700 determines a quantity of clusters using the frequency distribution function time evolution image (operation 1718). In some of these illustrative examples, method 1700 determines the quantity of clusters comprises determining the quantity of clusters by applying a singular value decomposition on the frequency distribution function time evolution image (operation 1720). In some of these illustrative examples, determining the quantity of clusters comprises selecting the quantity of clusters from entries within a curved portion of a plot of the singular values from the singular value decomposition on the frequency distribution function time evolution image (operation 1722).

Figure 18:
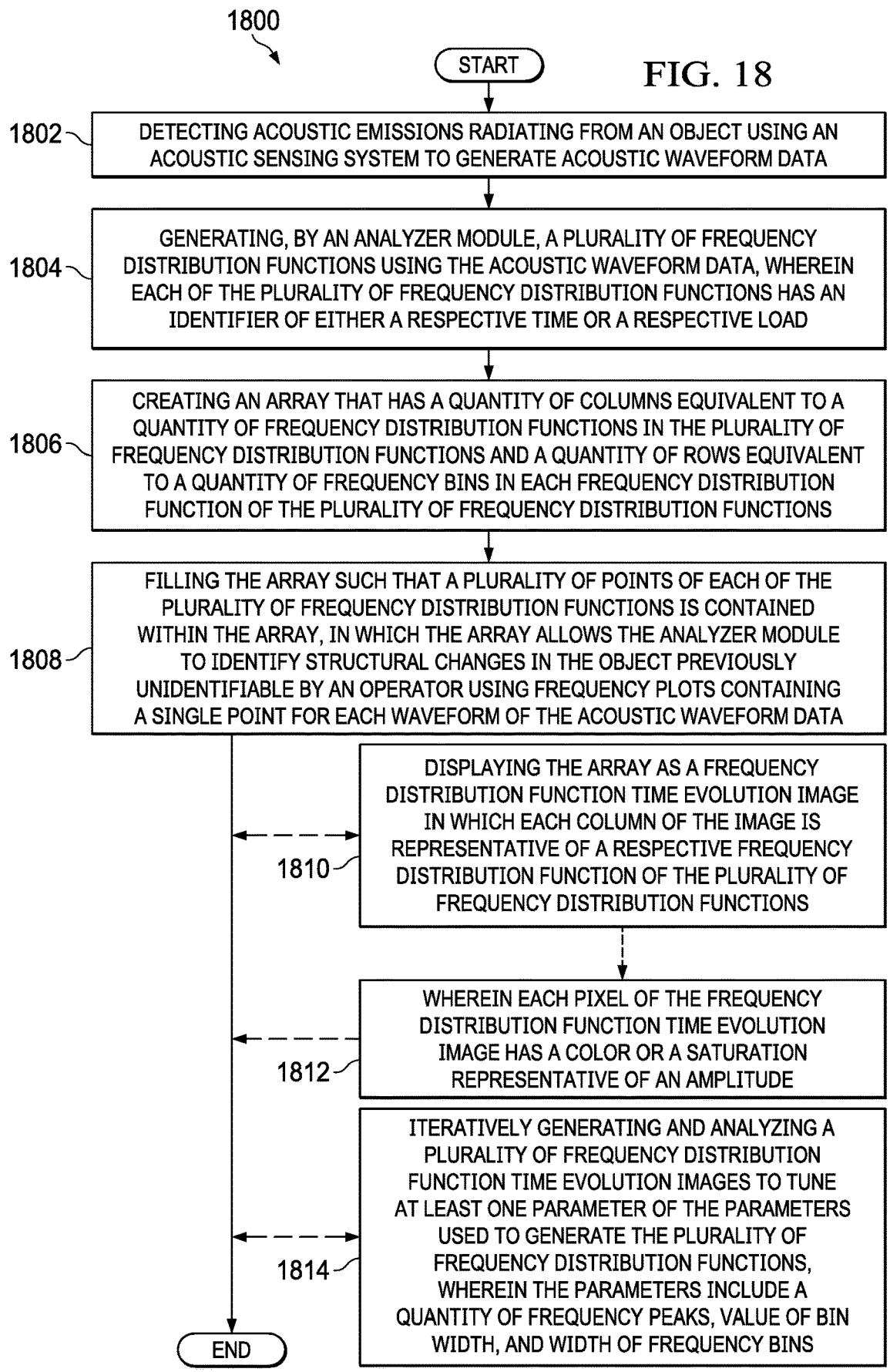
FIG. 18 is an illustration of a flowchart of a method for creating an array for analysis in accordance with an illustrative embodiment.

Turning now to FIG. 18, an illustration of a flowchart of a method for creating an array for analysis is depicted in accordance with an illustrative embodiment. Method 1800 may be implemented in test environment 100 of FIG. 1. Method 1800 may be implemented using acoustic sensing system 204 and analyzer module 214 of computer system 216 of FIGS. 2 and 13.

Method 1800 detects acoustic emissions radiating from an object using an acoustic sensing system to generate acoustic waveform data (operation 1802). Method 1800 generates, by an analyzer module, a plurality of frequency distribution functions using the acoustic waveform data, wherein each of the plurality of frequency distribution functions has an identifier of either a respective time or a respective load (operation 1804). Method 1800 creates an array that has a quantity of columns equivalent to a quantity of frequency distribution functions in the plurality of frequency distribution functions and a quantity of rows equivalent to a quantity of frequency bins in each frequency distribution function of the plurality of frequency distribution functions (operation 1806). Method 1800 fills the array such that a plurality of points of each of the plurality of frequency distribution functions is contained within the array, in which the array allows the analyzer module to identify structural changes in the object previously unidentifiable by an operator using frequency plots containing a single point for each waveform of the acoustic waveform data (operation 1808). Afterwards, method 1800 terminates.

In some illustrative examples, method 1800 fills the array such that all data of each of the plurality of frequency distribution functions is contained within the array. In some illustrative examples, method 1800 displays the array as a frequency distribution function time evolution image in which each column of the image is representative of a respective frequency distribution function of the plurality of frequency distribution functions (operation 1810). In some illustrative examples, in method 1800, each pixel of the frequency distribution function time evolution image has a color or a saturation representative of an amplitude (operation 1812). In some illustrative examples, method 1800 iteratively generates and analyzes a plurality of frequency distribution function time evolution images to tune at least one parameter of the parameters used to generate the plurality of frequency distribution functions, wherein the parameters include a quantity of frequency peaks, value of bin width, and width of frequency bins (operation 1814).

Figure 19:
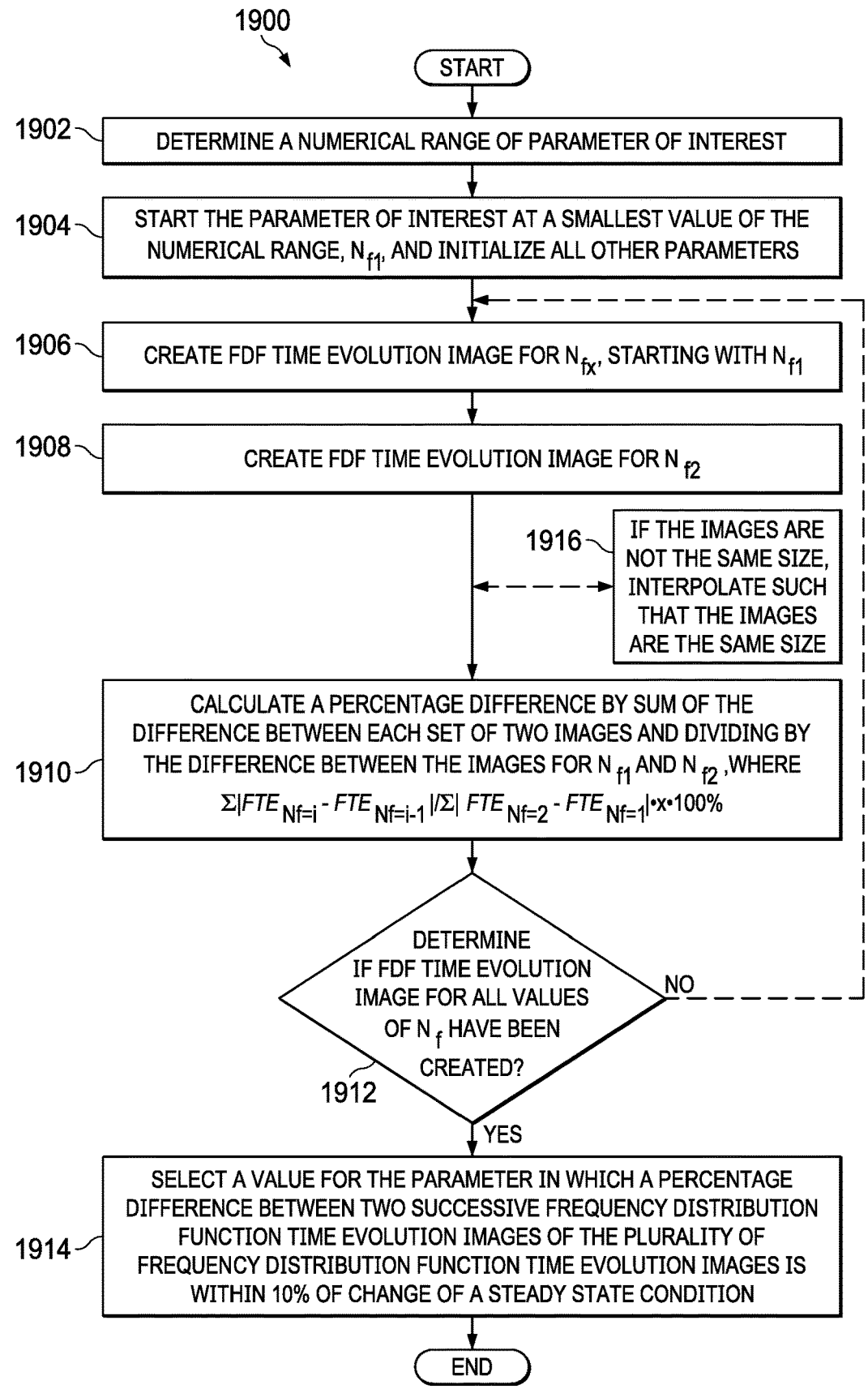
FIG. 19 is an illustration of a flowchart of a method for turning parameters in accordance with an illustrative embodiment.

Turning now to FIG. 19, an illustration of a flowchart of a method for turning parameters is depicted in accordance with an illustrative embodiment. Method 1900 may be implemented in test environment 100 of FIG. 1. Method 1900 may be implemented using acoustic sensing system 204 and analyzer module 214 of computer system 216 of FIGS. 2 and 13. Method 1900 is a method for tuning a parameter of interest. Any desirable parameter of width of frequency bins 1334, value of bin width 1336, or quantity of frequency peaks 1338 of FIG. 13 may be tuned using method 1900.

Method 1900 determines a numerical range of a parameter of interest (operation 1902). Method 1900 starts the parameter of interest at a smallest value of the numerical range, $N_{f1}$, and initialize all other parameters (operation 1904). Method 1900 creates a frequency distribution function time evolution image for $N_{fx}$, starting with $N_{f1}$ (operation 1906). Method 1900 creates a frequency distribution function time evolution image for $N_{f2}$ (operation 1908).

Method 1900 calculates a percentage difference by sum of the difference between each set of two images and dividing by the different between the images for $N_{f1}$ and $N_{f2}$, where $\Sigma|FTE_{Nf=i}-FTE_{Nf=i-1}|/\Sigma|FTE_{Nf=2}-FTE_{Nf=1}|\times 100\%$ (operation 1910). Method 1900 determines if frequency distribution function time evolution images for all values of $N_f$ have been created (operation 1912). If not, operations 1906 and 1908 are repeated until all values of $N_f$ have a frequency distribution function time evolution image. Method 1900 selects a value for the parameter in which a percentage difference between two successive frequency distribution function time evolution images of the plurality of frequency distribution function time evolution images is within 10% of change of a steady state condition (operation 1914). Afterwards, method 1900 terminates.

In some illustrative examples, if the images are not the same size, method 1900 interpolates such that the images are the same size (operation 1916).

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added, in addition to the illustrated blocks, in a flowchart or block diagram.

In some illustrative examples, not all blocks of method 1700, method 1800, or method 1900 are performed. For example, operations 1710 through 1722 of FIG. 17 are optional. As another example, operations 1810 through 1814 of FIG. 18 are optional. As a further example, operation 1916 of FIG. 19 is optional.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   an acoustic sensing system positioned relative to an object, wherein the acoustic sensing system detects acoustic emissions and generates acoustic waveform data for the acoustic emissions detected; and
   an analyzer module implemented in a computer system that receives load data and the acoustic waveform data for the object, generates a plurality of frequency distribution functions using the acoustic waveform data, and generates a frequency distribution function time evolution image from an array containing a plurality of points of each of the plurality of frequency distribution functions, wherein the array has a quantity of columns equivalent to a quantity of frequency distribution functions in the plurality of frequency distribution functions and a quantity of rows equivalent to a quantity of frequency bins in each frequency distribution function of the plurality of frequency distribution functions.

2. The apparatus of claim 1, wherein generating the frequency distribution function time evolution image allows an operator to assess a structural integrity of the object.

3. The apparatus of claim 1, wherein the analyzer module identifies a value of bin width for a plurality of bins for the plurality of frequency distribution functions wherein the value of bin width is either a defined time interval or a defined load interval.

4. The apparatus of claim 3, wherein the analyzer module identifies the value of bin width using iterative parameter tuning and a plurality of frequency distribution function time evolution images generated from the acoustic waveform data.

5. The apparatus of claim 4, wherein the analyzer module identifies the value of bin width when a percentage difference between two successive frequency distribution function time evolution images of the plurality of frequency distribution function time evolution images is within 10% of change of a steady state condition.

6. The apparatus of claim 1, wherein the analyzer module identifies at least one of a width of frequency bins or a quantity of frequency peaks using iterative parameter tuning and a plurality of frequency distribution function time evolution images generated from the acoustic waveform data.

7. The apparatus of claim 1, wherein the analyzer module determines a quantity of clusters using the frequency distribution function time evolution image.

8. The apparatus of claim 7, wherein the analyzer module determines the quantity of clusters by applying a singular value decomposition on the frequency distribution function time evolution image.

9. The apparatus of claim 8, wherein the quantity of clusters is selected from entries within a curved portion of a plot of the singular values from the singular value decomposition on the frequency distribution function time evolution image.

10. A method for analyzing an object using acoustic waves, the method comprising:
    receiving load data for the object;
    receiving acoustic waveform data for the object from an acoustic sensing system, wherein the acoustic waveform data represents acoustic emissions emanating from the object and is detected using the acoustic sensing system;
    generating a plurality of frequency distribution functions using the acoustic waveform data; and
    generating a frequency distribution function time evolution image from an array containing a plurality of points of each of the plurality of frequency distribution functions, wherein the array has a quantity of columns equivalent to a quantity of frequency distribution functions in the plurality of frequency distribution functions and a quantity of rows equivalent to a quantity of frequency bins in each frequency distribution function of the plurality of frequency distribution functions.

11. The method of claim 10, wherein the frequency distribution function time evolution image allows an operator to assess a structural integrity of the object.

12. The method of claim 10 further comprising:
    identifying a value of bin width for a plurality of bins for the plurality of frequency distribution functions, wherein the value of bin width is either a defined time interval or a defined load interval.

13. The method of claim 12, wherein identifying the value of bin width for the plurality of bins for the plurality of frequency distribution functions comprises identifying the value of bin width using iterative parameter tuning and a plurality of frequency distribution function time evolution images generated from the acoustic waveform data.

14. The method of claim 13, wherein identifying the value of bin width for the plurality of bins for the plurality of frequency distribution functions comprises identifying the value of bin width when a percentage difference between two successive frequency distribution function time evolution images of the plurality of frequency distribution function time evolution images is within 10% of change of a steady state condition.

15. The method of claim 10 further comprising:
    identifying at least one of a width of frequency bins or a quantity of frequency peaks using iterative parameter tuning and a plurality of frequency distribution function time evolution images generated from the acoustic waveform data.

16. The method of claim 10 further comprising:
   determining a quantity of clusters using the frequency distribution function time evolution image.

17. The method of claim 16, wherein determining the quantity of clusters comprises determining the quantity of clusters by applying a singular value decomposition on the frequency distribution function time evolution image.

18. The method of claim 17, wherein determining the quantity of clusters comprises selecting the quantity of clusters from entries within a curved portion of a plot of the singular values from the singular value decomposition on the frequency distribution function time evolution image.

19. A method comprising:
   detecting acoustic emissions radiating from an object using an acoustic sensing system to generate acoustic waveform data;
   generating, by an analyzer module, a plurality of frequency distribution functions using the acoustic waveform data, wherein each of the plurality of frequency distribution functions has an identifier of either a respective time or a respective load;
   creating an array that has a quantity of columns equivalent to a quantity of frequency distribution functions in the plurality of frequency distribution functions and a quantity of rows equivalent to a quantity of frequency bins in each frequency distribution function of the plurality of frequency distribution functions; and
   filling the array such that a plurality of points of each of the plurality of frequency distribution functions is contained within the array, in which the array allows the analyzer module to identify structural changes in the object previously unidentifiable by an operator using frequency plots containing a single point for each waveform of the acoustic waveform data.

20. The method of claim 19 further comprising:
   displaying the array as a frequency distribution function time evolution image in which each column of the frequency distribution function time evolution image is representative of a respective frequency distribution function of the plurality of frequency distribution functions.

21. The method of claim 20, wherein each pixel of the frequency distribution function time evolution image has a color or a saturation representative of an amplitude.

22. The method of claim 19 further comprising:
   iteratively generating and analyzing a plurality of frequency distribution function time evolution images to tune at least one parameter of the parameters used to generate the plurality of frequency distribution functions, wherein the parameters include a quantity of frequency peaks, value of bin width, and width of frequency bins.

* * * * *